United States Patent
Balmforth et al.

(10) Patent No.: US 11,332,780 B2
(45) Date of Patent: May 17, 2022

(54) SIMPLIFIED POLYNUCLEOTIDE SEQUENCE DETECTION METHOD

(71) Applicant: BIOFIDELITY LTD, Cambridge (GB)

(72) Inventors: Barnaby Balmforth, Cambridge (GB); Magdalena Stolarek-Januszkiewicz, Cambridge (GB); Ana Silva-Weatherley, Cambridge (GB); Paulina Powalowska, Cambridge (GB)

(73) Assignee: BIOFIDELITY LTD, Cambridge (GB)

( * ) Notice: Subject to any disclaimer, the term of this patent is extended or adjusted under 35 U.S.C. 154(b) by 0 days.

(21) Appl. No.: 16/911,762

(22) Filed: Jun. 25, 2020

(65) Prior Publication Data
US 2021/0189478 A1 Jun. 24, 2021

(30) Foreign Application Priority Data
Dec. 23, 2019 (GB) ..................................... 1919186

(51) Int. Cl.
*C12Q 1/6853* (2018.01)
*C12Q 1/6818* (2018.01)

(52) U.S. Cl.
CPC ......... *C12Q 1/6853* (2013.01); *C12Q 1/6818* (2013.01); *C12Q 2565/40* (2013.01); *C12Q 2600/16* (2013.01)

(58) Field of Classification Search
CPC .............................. C12Q 1/6853; C12Q 1/6818
See application file for complete search history.

(56) References Cited

U.S. PATENT DOCUMENTS

| | | | |
|---|---|---|---|
| 5,849,497 A | 12/1998 | Steinman | |
| 2006/0110765 A1 | 5/2006 | Wang | |
| 2006/0234252 A1 | 10/2006 | Andersen | |
| 2007/0154914 A1 | 7/2007 | Gelfand et al. | |
| 2009/0239283 A1 | 9/2009 | Liu et al. | |
| 2010/0112556 A1 | 5/2010 | Sampson et al. | |
| 2010/0112565 A1 | 5/2010 | Tobler | |
| 2018/0080074 A1 | 3/2018 | Balmforth et al. | |

FOREIGN PATENT DOCUMENTS

| | | |
|---|---|---|
| CN | 105483117 A | 4/2016 |
| CN | 108103159 A | 6/2018 |
| EP | 1627924 A1 | 2/2006 |
| EP | 2733221 A1 | 5/2014 |
| EP | 3207982 A1 | 8/2017 |
| EP | 3211092 A1 | 8/2017 |
| EP | 3447152 A1 | 2/2019 |
| WO | WO 2000/49180 A1 | 8/2000 |
| WO | WO 2001006295 A2 | 1/2001 |
| WO | WO 2003/095664 A2 | 11/2003 |
| WO | WO 2009019008 A1 | 2/2009 |
| WO | WO 2012032510 A1 | 3/2012 |
| WO | WO 2014/165210 A2 | 10/2014 |
| WO | WO 2014160199 A1 | 10/2014 |
| WO | WO 2014167323 A1 | 10/2014 |
| WO | WO 2015058176 A1 | 4/2015 |
| WO | WO 2015121675 A1 | 8/2015 |
| WO | WO 2018/210823 A1 | 11/2018 |
| WO | WO 2020/016590 A1 | 1/2020 |

OTHER PUBLICATIONS

Deutscher, M. P. et al., "Enzymatic Synthesis of Deoxyribonucleic Acid," *The Journal of Biological Chemistry*, vol. 244, pp. 3019-3028 (1969).
Reed, G. H. et al., "High-resolution DNA melting analysis for simple and efficient molecular diagnostics," *Pharmacogenomics*, vol. 8, pp. 597-608 (2007).
R. Ingram et al., "PAP-LMPCR for improved, allele-specific footprinting and automated chromatin fine structure analysis," Nucleic Acids Research, vol. 36, No. 3, e19, pp. 1-8 (Jan. 2008).
Barken, K. B. et al., "Effect of unlabeled helper probes on detection of an RNA target by bead-based sandwich hybridization," *BioTechniques*, vol. 36, pp. 124-132 (2004).
Berti, F. et al., "Microfluidic-based electrochemical genosensor coupled to magnetic beads for hybridization detection," *Talanta*, vol. 77, pp. 971-978 (2009).
Cansiz, S. et al., "A sandwich-type DNA array platform for detection of GM targets in multiplex assay," *European Food Research and Technology*, vol. 235, pp. 429-437 (2012).
Harrison, A. et al., "DNA Methylation: a Timeline of Methods and Applications," *Frontiers in Genetics*, vol. 2, p. 3 (2011).
Lagunavicius, A. et al., "Duality of polynucleotide substrates for Phi29 DNA polymerase," *RNA*, vol. 14, pp. 503-513 (2008).
Liu, Q. et al., "Pyrophosphorolysis-Activated Polymerization (PAP): Application to Allele-Specific Amplification," *BioTechniques*, vol. 29, pp. 1072-1083 (2000).
Liu, Q. et al., "PAP: Detection of Ultra Rare Mutations Depends on P* Oligonucleotides: "Sleeping Beauties" Awakened by the Kiss of Pyrophosphorolysis," *Human mutations*, vol. 23, pp. 426-436 (2004).

(Continued)

*Primary Examiner* — Samuel C Woolwine
*Assistant Examiner* — Carolyn L Greene
(74) *Attorney, Agent, or Firm* — Bookoff McAndrews, PLLC

(57) ABSTRACT

Methods of detecting target polynucleotide sequences may include introducing one or more nucleic acid analytes to a first reaction mixture comprising a single-stranded probe oligonucleotide $A_0$, a pyrophosphorolysing enzyme, and a ligase. The analyte may anneal to the single-stranded probe oligonucleotide $A_0$ to create a first intermediate product which is at least partially double-stranded, where the 3' end of $A_0$ forms a double-stranded complex with the analyte and where $A_0$ is pyrophosphorylsed in the 3'-5' direction from the 3' end to create at least a partially digested strand $A_1$. $A_1$ may undergo ligation to form oligonucleotide $A_2$. The methods may also include detecting a signal derived from the formed oligonucleotides, and inferring therefrom the presence or absence of the target polynucleotide sequence in the analyte.

30 Claims, 10 Drawing Sheets
Specification includes a Sequence Listing.

(56) References Cited

OTHER PUBLICATIONS

Silva, A. et al., "Single-copy detection of somatic variants from solid and liquid biopsy," *Scientific reports*, vol. 11, No. 6068 (2021).
Van Den Oever, J. M. E. et al., "Mrassf1a-Pap, a Novel Methylation-Based Assay for the Detection of Cell-Free Fetal DNA in Maternal Plasma," *PLS ONE*, vol. 8, No. 12 (2013).

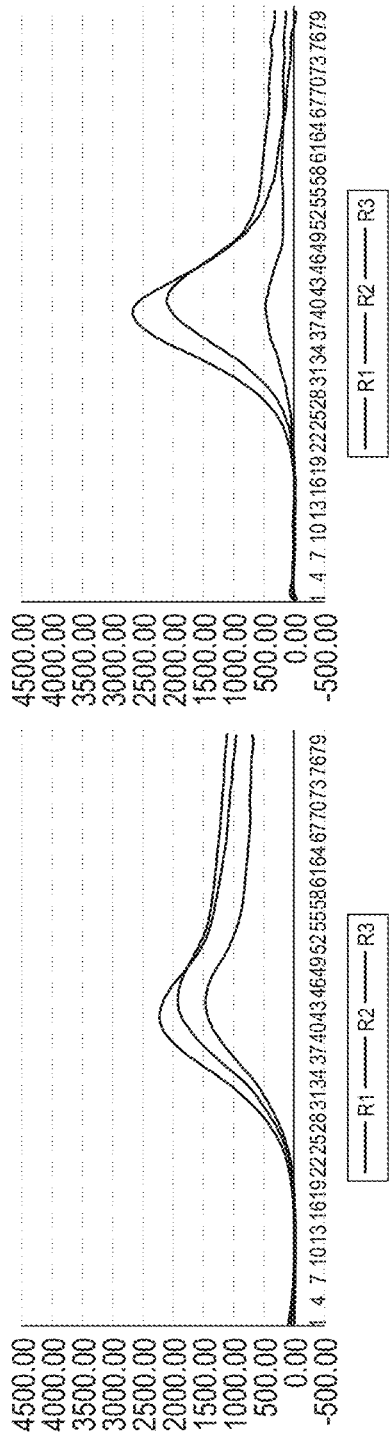
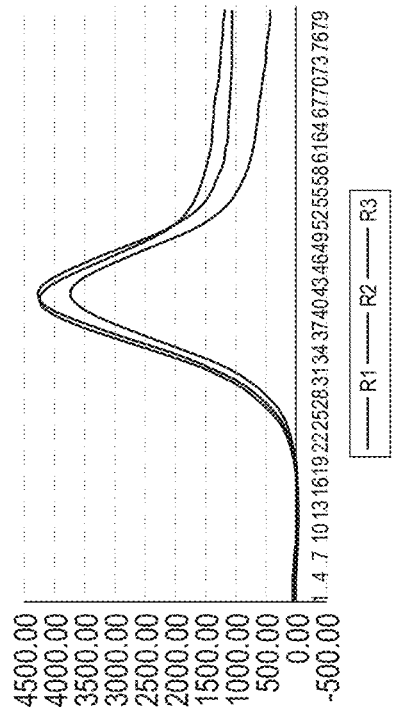
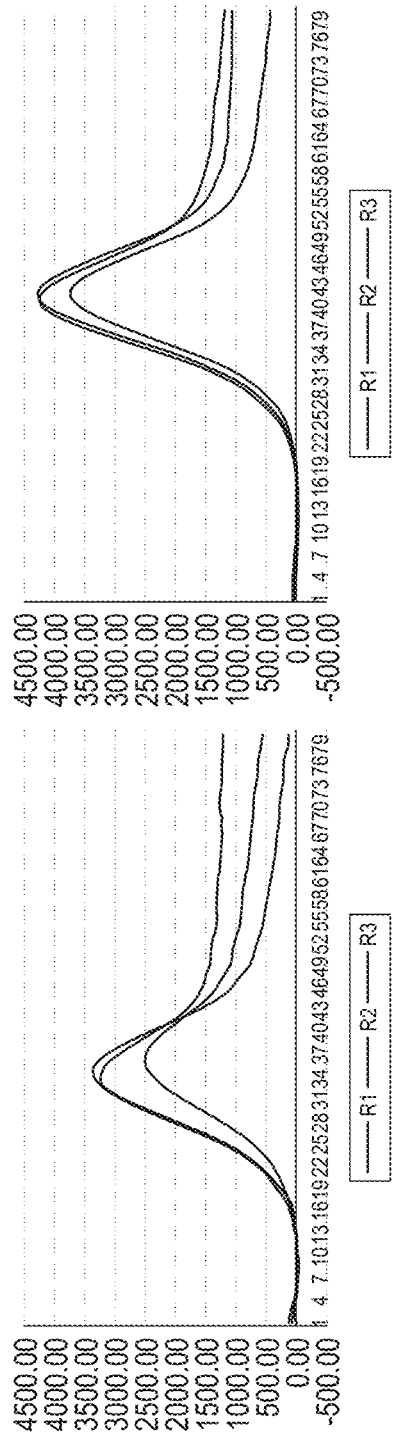
Fig. 4(A) Fig. 4(B) Fig. 4(C) Fig. 4(D)

SIMPLIFIED POLYNUCLEOTIDE SEQUENCE DETECTION METHOD

CROSS-REFERENCE TO RELATED APPLICATIONS

This application claims priority to United Kingdom Application No. GB 1919186.5, filed on Dec. 23, 2019, which is hereby incorporated by reference in its entirety.

SEQUENCE LISTING

This application contains a sequence listing, submitted electronically in ASCII format under the filename Sequence_Listing.txt, which is incorporated by reference herein in its entirety. The ASCII copy of the sequence listing was created on Jul. 24, 2020, and is 1,689 bytes in size.

This invention relates to a simplified polynucleotide sequence detection method suitable for testing for the presence of a large number of diagnostic markers, including those used in the identification of cancer, infectious disease and transplant organ rejection. It is also useful for companion diagnostic testing in which a panel of markers must be identified reliably and at low cost.

The polymerase chain reaction (PCR) is a well-known and powerful technique for amplifying DNA or RNA present in laboratory and diagnostic samples to a point where they can be reliably detected and/or quantified. However, when applied for the purposes of investigating analyte samples containing low-levels of such molecules, it suffers from a number of limitations. First, whilst the technique can detect as little as a single target molecule, it is prone to generating false positive results due to unwanted amplification of other nucleic acid sequences present in the sample. This makes the choice of oligonucleotide primers used to initiate the reaction key; which in turn makes designing primers with the required level of specificity relatively complex. As a consequence, many PCR-based tests available on the market today have limited specificity.

A second drawback is that multiplexing of PCR-based methods is in practice limited to at most tens of target sequences (frequently no more than 10) with the avoidance of primer-primer interactions resulting in the need for relatively narrow operational windows.

Another issue is that, because the PCR reaction cycles in an exponential fashion, quantification of the target is difficult; small variations in the efficiency of the reaction having a huge impact on the amount of detectable material generated. Even with appropriate controls and calibrations in place, quantification is thus typically limited to an accuracy within a factor of around 3.

Finally, mutations in the region targeted for investigation by PCR amplification methods can have unwanted side effects. For example, there have been instances where FDA-approved tests have had to be withdrawn because the target organism underwent mutation in the genetic region targeted by the test primers resulting in large numbers of false negatives. Conversely, if a specific single nucleotide polymorphism (SNP) is targeted for amplification the PCR method will often give a false positive when the wild-type variant is present. Avoiding this requires very careful primer design and further limits the efficacy of multiplexing. This is particularly relevant when searching for panels of SNPs as is a common requirement in cancer testing/screening or companion diagnostics.

SUMMARY OF INVENTION

We have now developed a new simplified method which builds on our experience using the pyrophosphorolysis method employed in our earlier patent (PCT/GB2019/052017, published as WO 2020/016590) to overcome many of these limitations. In doing so, it harnesses the double-strand specificity of pyrophosphorolysis; a reaction which will not proceed efficiently with single-stranded oligonucleotide substrates or double-stranded substrates which include blocking groups or nucleotide mismatches. The new method is faster, less complex and less expensive to run than that disclosed in PCT/GB2019/052017. Thus, according to the present invention, there is provided a method of detecting a target polynucleotide sequence in a given nucleic acid analyte, the method comprising the steps of:

(a) introducing one or more nucleic acid analytes to a first reaction mixture comprising:
  i. a single-stranded probe oligonucleotide $A_0$;
  ii. a pyrophosphorolysing enzyme; and
  iii. a ligase wherein $A_0$ is pyrophosphorylsed in the 3'-5' direction from the 3' end to create at least a partially digested strand $A_1$ and $A_1$ undergoes ligation to form $A_2$;

(b) detecting a signal derived from the products of the previous step, wherein the products are $A_2$ or a portion thereof, or multiple copies of $A_2$ or multiple copies of a portion thereof, and inferring therefrom the presence or absence of the polynucleotide target sequence in the analyte.

The analytes to which the method of the invention can be applied are those nucleic acids, such as naturally-occurring or synthetic DNA or RNA molecules, which include the target polynucleotide sequence(s) being sought. In one embodiment, the analyte will typically be present in an aqueous solution containing it and other biological material and in one embodiment the analyte will be present along with other background nucleic acid molecules which are not of interest for the purposes of the test. In some embodiments, the analyte will be present in low amounts relative to these other nucleic acid components. Preferably, for example where the analyte is derived from a biological specimen containing cellular material, prior to performing step (a) of the method some or all of these other nucleic acids and extraneous biological material will have been removed using sample-preparation techniques such as filtration, centrifuging, chromatography or electrophoresis. Suitably, the analyte is derived from a biological sample taken from a mammalian subject (especially a human patient) such as blood, plasma, sputum, urine, skin or a biopsy. In one embodiment, the biological sample will be subjected to lysis in order that the analyte is released by disrupting any cells present. In other embodiments, the analyte may already be present in free form within the sample itself; for example cell-free DNA circulating in blood or plasma.

BRIEF DESCRIPTION OF DRAWINGS

FIG. 3(A) shows detection of 1% MAF T790M using Mako, Klenow and Bsu. FIG. 3(B) shows the detection of 0.5% MAF T790M using Bst LF at a range of different $P_{pi}$ concentrations. All four enzymes performed very well even without extended optimisation.

FIGS. 4(A)-4(D): Results for the detection of 1% MAF, T790M, using the methods of Protocol 4 of the current invention using four different pyrophosphorylising (PPL) enzymes: Mako, Klenow, Bsu and Bst LF.

DESCRIPTION OF EMBODIMENTS

Figure 1:
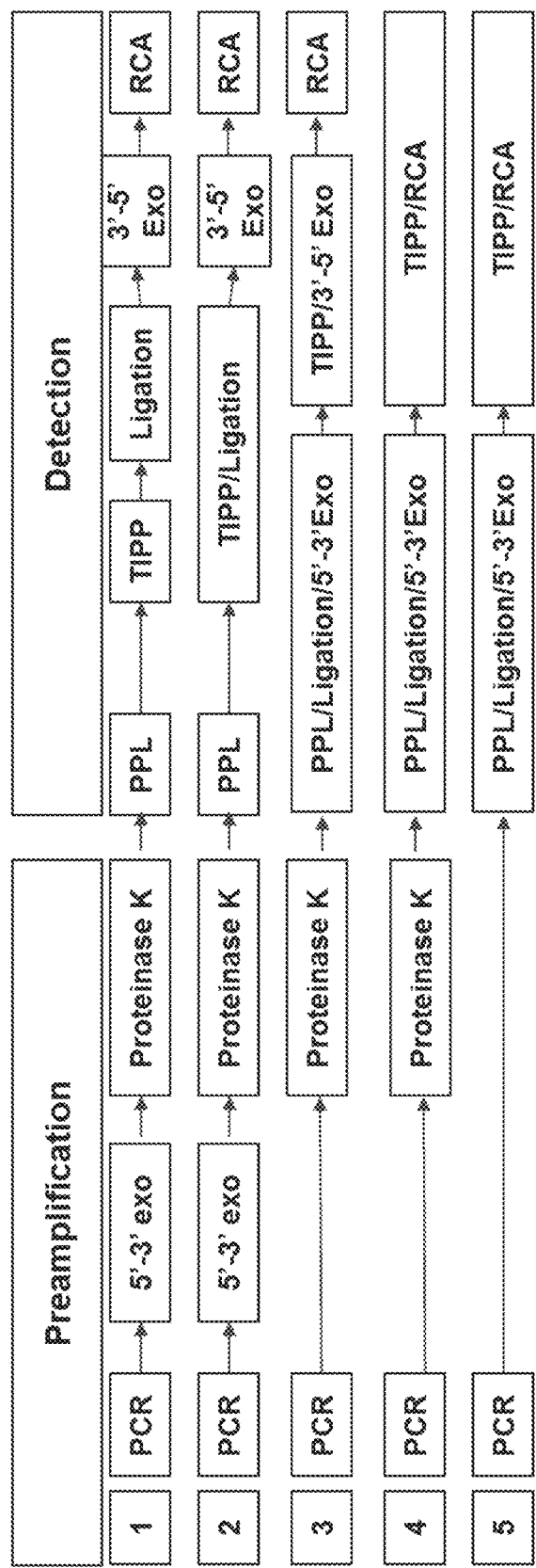
FIG. 1: Protocols for simplified polynucleotide sequence detection methods.

In an aspect of the present invention, there is provided a method of detecting a target polynucleotide sequence in a given nucleic acid analyte present in a sample, the method comprising the steps of:
(a) introducing one or more nucleic acid analytes to a first reaction mixture comprising:
i. a single-stranded probe oligonucleotide $A_0$;
ii. a pyrophosphorolysing enzyme; and
iii. a ligase
wherein $A_0$ is pyrophosphorylsed in the 3'-5' direction from the 3' end to create at least a partially digested strand $A_1$ and $A_1$ undergoes ligation to form $A_2$;
(b) detecting a signal derived from the products of the previous step, wherein the products are $A_2$ or a portion thereof, or multiple copies of $A_2$ or multiple copies of a portion thereof, and inferring therefrom the presence or absence of the polynucleotide target sequence in the analyte.

In some embodiments, the first reaction mixture further comprises a source of pyrophosphate ions.

In some embodiments, the first reaction mixture further comprises at least one single-stranded primer oligonucleotide that is substantially complementary to a portion of $A_0$ and deoxyribonucleotide triphosphates (dNTPs).

In some embodiments, the first reaction mixture further comprises an amplification enzyme.

In some embodiments, the products of step (a) are introduced to a second reaction mixture prior to step (b), said second reaction mixture comprising at least one single-stranded primer oligonucleotide and dTNPs.

In some embodiments, the second reaction mixture further comprises an amplification enzyme.

In some embodiments, one or more nucleic acid analytes may be introduced to a first and second reaction mixture concurrently.

In some embodiments, one or more nucleic acid analytes may be introduced to a first and second reaction mixture consecutively.

In some embodiments, the dNTPs are hot start dNTPs.

In some embodiments, during step (a) the analyte anneals to the single-stranded probe oligonucleotide $A_0$ to create a first intermediate product which is at least partially double-stranded and in which the 3' end of $A_0$ forms a double-stranded complex with the analyte target sequence.

In some embodiments, during step (a) the first intermediate product is pyrophosphorolysed in the 3'-5' direction from the 3' end of $A_0$ to create partially digested strand $A_1$ and the analyte.

In some embodiments, the first reaction mixture further comprises a ligation probe oligonucleotide C and the partially digested strand $A_1$ is ligated at the 3' end to the 5' end of C to create an oligonucleotide $A_2$.

In some embodiments, the partially digested strand $A_1$ is circularised through ligation of its 3' and 5' ends.

In some embodiments, the ligation of $A_1$ occurs:
during step (a); or
during step (b); or
inbetween steps (a) and (b).

In some embodiments, the first reaction mixture further comprises a 5'-3' exonuclease and the 5' end of $A_0$ is rendered resistant to 5'-3' exonuclease digestion.

In some embodiments, after amplification of the given nucleic acid analyte and prior to addition of the first reaction mixture (step (a)), the sample is further treated with a proteinase.

In some embodiments, the first reaction mixture further comprises a phosphatase or phosphohydrolase.

In some embodiments, prior to or during step (b) the products of the previous step are treated with a pyrophosphatase.

In some embodiments, prior to or during step (b) the products of the previous step are treated with an exonuclease.

In some embodiments, the oligonucleotide C further comprises a 3' or internal modification protecting it from 3'-5' exonuclease digestion.

In some embodiments, the oligonucleotide C further comprises a 5' modification protecting it from 5'-3' exonuclease digestion.

In some embodiments, the first or second reaction mixture further comprises a splint oligonucleotide D.

In some embodiments, D comprises an oligonucleotide region complementary to the 3' end of $A_1$ and a region complementary to either the 5' end of oligonucleotide C or to the 5' end of $A_1$.

In some embodiments, D is unable to undergo extension against $A_1$ by virtue of either a 3' modification or through a mismatch between the 3' end of D and the corresponding region of $A_1$.

In some embodiments, the enzyme which performs pyrophosphorolysis of $A_0$ to form partially digested strand $A_1$ also amplifies $A_2$.

In some embodiments, detection is achieved using one or more oligonucleotide fluorescent binding dyes or molecular probes.

In some embodiments, an increase in signal over time resulting from the generation of amplicons of $A_2$ is used to infer the concentration of the target sequence in the analyte.

In some embodiments, multiple probes $A_0$ are employed, each selective for a different target sequence and each including an identification region, and further characterised in that the amplicons derived from $A_2$ include this identification region and therefore the target sequences present in the analyte are inferred through the detection of the identification region(s).

In some embodiments, detection of the identification regions(s) is carried out using molecular probes or through sequencing.

In some embodiments, the final step of the method further comprises the steps of:
  i. labelling the products of step (b) using one or more oligonucleotide fluorescent binding dyes or molecular probes;
  ii. measuring the fluorescent signal of the products;
  iii. exposing the products to a set of denaturing conditions; and
identifying the polynucleotide target sequence in the analyte by monitoring changes in the fluorescent signal of the products during exposure to the denaturing conditions.

In some embodiments, the one or more nucleic acid analytes are split into multiple reaction volumes, each volume having a one or more probe oligonucleotide $A_0$, introduced to detect different target sequences.

In some embodiments, the different probes $A_0$ comprise common priming sites, allowing a single or single set of primers to be used for amplification of a region of $A_2$.

In some embodiments, there is provided a method of detecting a target polynucleotide sequence in a given nucleic acid analyte present in a sample, the method comprising the steps of:
  (a) amplifying a given nucleic acid analyte present in the sample;
  (b) introducing the products of step (a) to a first reaction mixture comprising:
    i. a single-stranded probe oligonucleotide $A_0$;
    ii. a pyrophosphorolysing enzyme; and
    iii. a ligase
wherein $A_0$ is pyrophosphorylsed in the 3'-5' direction from the 3' end to create at least a partially digested strand $A_1$ and $A_1$ undergoes ligation to form $A_2$;
  (c) detecting a signal derived from the products of the previous step, wherein the products are $A_2$ or a portion thereof, or multiple copies of $A_2$ or multiple copies of a portion thereof, and inferring therefrom the presence or absence of the polynucleotide target sequence in the analyte.

According to the present invention, there are provided methods of detecting a target polynucleotide sequence in a given nucleic acid analyte. The analytes to which the various methods of the invention can be applied may be prepared from the biological sample mentioned above by a series of preliminary steps designed to amplify the analyte and separate if from the background genomic DNA which is typically present in significant excess. This method is generally applicable to the production of single-stranded target analytes and is therefore useful in situations other than when it is integrated with or further comprises part of the method of the first aspect of the invention. Accordingly, there is provided a method for preparing at least one single-stranded analyte of a nucleic acid comprised of a target polynucleotide region characterised by the steps of (1) producing amplicons of the analyte(s) by subjecting a biological sample comprised of the analyte(s) and optionally background genomic DNA to cycles of amplification. In one preferred embodiment amplification is carried out using the polymerase chain reaction (PCR) in the presence of a polymerase, nucleoside triphosphates and at least one corresponding primer pair wherein one of the primers includes a 5'-3' exonuclease blocking group and (2) optionally digesting the product of step (1) with an exonuclease having 5'-3' exonucleolytic activity. In one embodiment, the method may further comprise (3) reacting the product of step (2) with a proteinase to destroy the polymerase and thereafter (4) deactivating the proteinase by heating the product of step (3) to a temperature in excess of 50° C.

In one preferred embodiment steps (1) to (4) are carried out prior to step (a) of the method of the first aspect of the invention to produce an integrated method of detecting target sequences derived from a biological sample. In another embodiment, the biological sample has undergone cell lysis before step (1) is carried out.

In some embodiments of step (1) the nucleoside triphosphates are a mixture of the four deoxynucleoside triphosphates characteristic of naturally occurring DNA. In a preferred embodiment the mixture of deoxynucleoside triphosphates comprise deoxyuridine triphosphate (dUTP) instead of deoxythymidine triphosphate (dTTP) and step (1) is further carried out in the presence of the enzyme dUTP-DNA glycolase (UDG) to remove any contaminating amplicons from previous assays. In yet another embodiment, a high fidelity polymerase is used in step (1) for example one of those sold under the trade name Phusion® or Q5.

In some embodiments, the nucleoside triphosphates are a mixture of synthetic or modified deoxynucleoside triphosphates.

In some embodiments, the nucleoside triphosphates are a mixture of the four deoxynucleoside triphosphates and synthetic or modified deoxynucleotide triphosphates.

In some embodiments, step (1) is carried out using a limited amount of primer and an excess of amplification cycles. By this means a fixed amount of amplicons is produced regardless of the initial amount of analyte. Thus the need for analyte quantification prior to subsequent steps is avoided. In another embodiment of step (1), which has the advantage of obviating the need for step (2), amplification is carried out in the presence of a primer pair where one of the two primers is present in excess of the other, resulting in generation of single-stranded amplicons once one primer is fully utilised.

In one preferred embodiment of step (2), the 5' primer is blocked with an exonuclease blocking group selected from phosphorothioate linkages, inverted bases, DNA spacers and other oligonucleotide modifications commonly known in the art. In another embodiment the other primer in the pair has a phosphate group at its 5'end.

In some embodiments, in step (3) the proteinase employed is proteinase K and step (4) is carried out by heating to a temperature of 80 to 100° C. for up to 30 minutes. In one embodiment, in step (3) the proteinase employed is proteinase K, step (3) is carried out by heating to a temperature of 55° C. for 5 minutes and step (4) is carried out by heating to a temperature of 95° C. for 10 minutes. In another embodiment at some point after step (2) the reaction medium is treated with a phosphatase or phosphohydrolase to remove any residual nucleoside triphosphates which may be present.

In some embodiments, the target polynucleotide sequence in the analyte will be a gene or chromosomal region within the DNA or RNA of a cancerous tumour cell and will be characterised by the presence of one or more mutations; for example in the form of one or more single nucleotide polymorphisms (SNPs). Thus the invention will be useful in the monitoring of and/or treatment for disease recurrence. Patients who have been declared free of disease following treatment may be monitored over time to detect the recurrence of disease. This needs to be done non-invasively and requires sensitive detection of target sequences from blood samples. Similarly, for some cancers there are residual cancer cells that remain in a patient after treatment. Monitoring of the levels of these cells (or cell free DNA) present in the patient's blood, using the current invention, allows detection of recurrence of disease or failure of current therapy and the need to switch to an alternative.

In some embodiments, detection of the target polynucleotide sequence will allow repeated testing of patient samples during treatment of disease to allow early detection of developed resistance to therapy. For example, epidermal growth factor receptor (EGFR) inhibitors, such as gefitinib, erlotinib, are commonly used as first line treatments for non-small cell lung cancer (NSCLC). During treatment the tumour will often develop mutations in the EGFR gene (e.g T790M, C797S) which confer resistance to the treatment. Early detection of these mutations allows transfer of the patient onto alternative therapies.

In some embodiments, the target polynucleotide sequence in the analyte will be a gene or chromosomal region within the DNA or RNA of fetal origin and will be characterised by the presence of one or more mutations; for example in the form of one or more single nucleotide polymorphisms (SNPs). Thus, the invention may be used to detect mutations at very low allele fractions, at an earlier stage of pregnancy than other available testing techniques.

In another embodiment, the target polynucleotide sequence may be a gene or genomic region derived from an otherwise healthy individual but the genetic information obtained may assist in generating valuable companion diagnostic information allowing medical or therapeutic conclusions to be drawn across one or more defined groups within the human population.

In yet another embodiment, the target polynucleotide sequence may be characteristic of an infectious disease, or of resistance of an infectious disease to treatment with certain therapies; for example a polynucleotide sequence characteristic of a gene or chromosomal region of a bacterium or a virus, or a mutation therein conferring resistance to therapy.

In some embodiments, the target polynucleotide sequence may be characteristic of donor DNA. When a transplanted organ is rejected by the patient, the DNA from this organ is shed into the patient's bloodstream. Early detection of this DNA would allow early detection of rejection. This could be achieved using custom panels of donor-specific markers, or by using panels of variants known to be common in the population, some of which will be present in the donor and some in the recipient. Routine monitoring of organ recipients over time is thus enabled by the claimed method.

In yet another embodiment, various versions of the method using different combinations of probes (see below) are employed in parallel so that the analyte can be simultaneously screened for multiple target sequences; for example sources of cancer, cancer indicators or multiple sources of infection. In this approach, the amplified products obtained in by parallel application of the method are contacted with a detection panel comprised of one or more oligonucleotide binding dyes or sequence specific molecular probes such as a molecular beacon, hairpin probe or the like. Thus, in another aspect of the invention there is provided the use of at least one probe and optionally one ligation oligonucleotide in combination with one or more chemical and biological probes selective for the target polynucleotide sequences or with the use of sequencing to identify the amplified probe regions.

In some embodiments, the single-stranded probe oligonucleotide $A_0$ comprises a priming region and a 3' end which is complementary to the target polynucleotide sequence to be detected. By this means, a first intermediate product is created which is at least partially double-stranded. In one embodiment, this step is carried out in the presence of excess $A_0$ and in an aqueous medium containing the analyte and any other nucleic acid molecules.

During step (a), the double-stranded region of the first intermediate product is pyrophosphorolysed in the 3'-5' direction from the 3' end of its $A_0$ strand. As a consequence, the $A_0$ strand is progressively digested to create a partially digested strand; hereinafter referred to as $A_1$. Where the probe oligonucleotide erroneously hybridises with a non-target sequence, the pyrophosphorolysis reaction will stop at any mismatches, preventing subsequent steps of the method from proceeding. In another embodiment, this digestion continues until $A_1$ lacks sufficient complementarity with the analyte or a target region therein to form a stable duplex. At this point, the various strands then separate by melting, thereby producing $A_1$ in single-stranded form. Under typical pyrophosphorolysis conditions, this separation occurs when there are between 6 and 20 complementary nucleotides between the analyte and $A_0$.

Suitably, pyrophosphorolysis is carried out in the reaction medium at a temperature in the range 20 to 90° C. in the presence of at least a polymerase exhibiting pyrophosphorolysis activity and a source of pyrophosphate ion. Further information about the pyrophosphorolysis reaction as applied to the digestion of polynucleotides can be found for example in J. Biol. Chem. 244 (1969) pp. 3019-3028 or our earlier patent application.

In some embodiments, the pyrophosphorolysis step is driven by the presence of a source of excess polypyrophosphate, suitable sources including those compounds containing 3 or more phosphorous atoms.

In some embodiments, the first reaction mixture comprises a source of excess polypyrophosphate.

In some embodiments, the pyrophosphorolysis step is driven by the presence of a source of excess modified pyrophosphate. Suitable modified pyrophosphates include those with other atoms or groups substituted in place of the bridging oxygen, or pyrophosphate (or polypyrophosphate) with substitutions or modifying groups on the other oxygens. The person skilled in the art will understand that there are many such examples of modified pyrophosphate which would be suitable for use in the current invention, a non-limiting selection of which are:

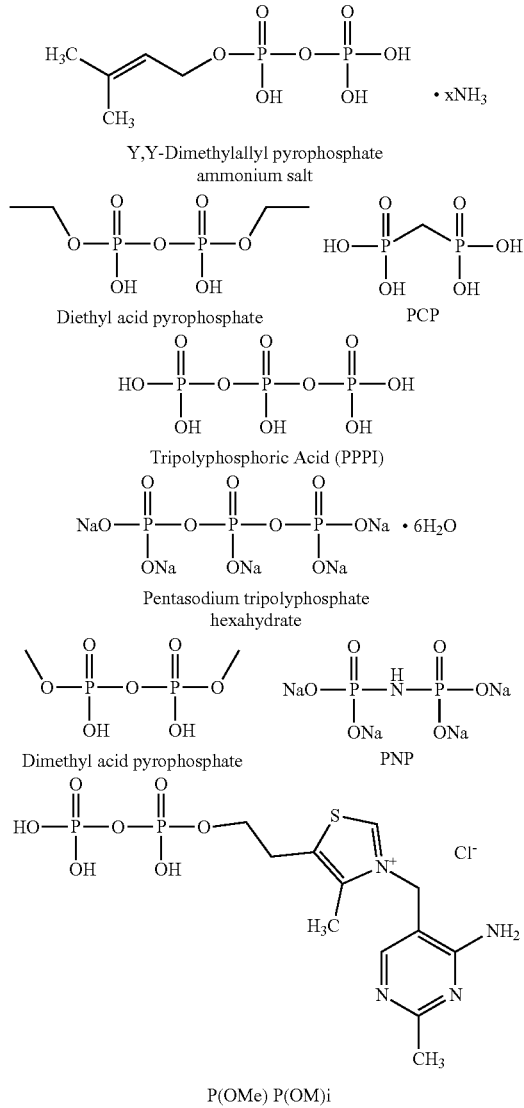

In some embodiments, the first reaction mixture comprises a source of excess modified polypyrophosphate.

In one preferred embodiment, the source of pyrophosphate ion is PNP, PCP or Tripolyphoshoric Acid (PPPi).

Further, but not limiting, examples of sources of pyrophosphate ion for use in the pyrophosphorolysis step (b) may be found in WO2014/165210 and WO00/49180.

In some embodiments, the source of excess modified pyrophosphate can be represented as Y—H wherein Y corresponds to the general formula (X—O)$_2$P(=B)—(Z—P(=B)(O—X))$_n$— wherein n is an integer from 1 to 4; each Z— is selected independently from —O—, —NH— or —CH$_2$—; each B is independently either O or S; the X groups are independently selected from —H, —Na, —K, alkyl, alkenyl, or a heterocyclic group with the proviso that when both Z and B correspond to —O— and when n is 1 at least one X group is not H.

In some embodiments, Y corresponds to the general formula (X—O)$_2$P(=B)—(Z—P(=B)(O—X))$_n$— wherein n is 1, 2, 3 or 4. In another embodiment, the Y group corresponds to the general formula (X—O)$_2$P(=O)—Z—P(=O)(O—H)— wherein one of the X groups is —H. In yet another preferred embodiment, Y corresponds to the general formula (X—O)$_2$P(=O)—Z—P(=O)(O—X)— wherein at least one of the X groups is selected from methyl, ethyl, allyl or dimethylallyl.

In an alternative embodiment, Y corresponds to either of the general formulae (H—O)$_2$P(=O)—Z—P(=O)(O—H)— wherein Z is either —NH— or —CH$_2$— or (X—O)$_2$P(=O)—Z—P(=O)(O—X)— wherein the X groups are all either —Na or —K and Z is either —NH— or —CH$_2$—.

In another embodiment, Y corresponds to the general formula (H—O)$_2$P(=B)—O—P(=B)(O—H)— wherein each B group is independently either O or S, with at least one being S.

Specific examples of preferred embodiments of Y include those of the formula (X1—O)(HO)P(=O)—Z—P(=O)(O—X2) wherein Z is O, NH or CH$_2$ and (a) X1 is γ,γ-dimethylallyl, and X2 is —H; or (b) X1 and X2 are both methyl; or (c) X1 and X2 are both ethyl; or (d) X1 is methyl and X2 is ethyl or vice versa.

In some embodiments, where molecular probes are to be used for detection, the probe oligonucleotide A$_0$ is configured to include an oligonucleotide identification region on the 5' side of the region complementary to the target sequence, and the molecular probes employed are designed to anneal to this identification region. In one embodiment, only the 3' region of A$_0$ is able to anneal to the target; i.e. any other regions lack sufficient complementarity with the analyte for a stable duplex to exist at the temperature at which the pyrophosphorolysis step is carried out. Here and throughout, by the term 'sufficient complementarity' is meant that, to the extent that a given region has complementarity with a given region on the analyte, the region of complementarity is more than 10 nucleotides long.

In a further aspect of the methods of the invention there is provided alternate embodiments in which the phosphorolysis step of any previous embodiment is replaced with an exonuclease digestion step using a double-strand specific exonuclease. The person skilled in the art will understand that double-strand specific exonucleases include those that read in the 3'-5' direction, such as ExoIII, and those that read in the 5'-3' direction, such as Lambda Exo, amongst many others.

In some embodiments of the invention wherein the exonuclease digestion step utilises a double strand-specific 5'-3' exonuclease, it is the 5' end of A$_0$ that is complementary to the target analyte and the common priming sequence and blocking group are located on the 3' side of the region complementary to the target. In a further embodiment, where molecular probes are to be used for detection the probe oligonucleotide A$_0$ is configured to include an oligonucleotide identification region on the 3' side of the region complementary to the target sequence, and the molecular probes employed are designed to anneal to this identification region.

In embodiments of the invention wherein the exonuclease digestion step utilises a double strand-specific 5'-3' exonuclease, an exonuclease having 3' to 5' exonucleolytic activity can optionally be added to the first reaction mixture for the purpose of digesting any other nucleic acid molecules present whilst leaving A$_0$ and any material comprising partially digested strand A$_1$ intact. Suitably, this resistance to exonucleolysis is achieved as described elsewhere in this application.

In one preferable embodiment of the invention, the 5' end of A$_0$ or an internal site on the 5' side of the priming region is rendered resistant to exonucleolysis. By this means and after, or simultaneously with, the pyrophosphorolysis step, an exonuclease having 5'-3' exonucleolytic activity can optionally be added to the reaction medium for the purpose of digesting any other nucleic acid molecules present whilst leaving $A_0$ and any material comprising the partially digested strand $A_1$ intact. Suitably, this resistance to exonucleolysis is achieved by introducing one or more blocking groups into the oligonucleotide $A_0$ at the required point. In one embodiment, these blocking groups may be selected from phosphorothioate linkages and other backbone modifications commonly used in the art, C3 spacers, phosphate groups, modified bases and the like.

In some embodiments, the identification region will comprise or have embedded within a barcoding region which has a unique sequence and is adapted to be indirectly identified using a sequence-specific molecular probe applied to the amplified components $A_2$ or directly by the sequencing of these components. Examples of molecular probes which may be used include, but are not limited to, molecular beacons, TaqMan® probes, Scorpion® probes and the like.

In all embodiments the $A_2$ strand or a desired region thereof is caused to undergo amplification so that multiple, typically many millions, of copies are made. This is achieved by priming a region of $A_2$ and subsequently any amplicons derived therefrom with single-stranded primer oligonucleotides, provided for example in the form of a forward/reverse or sense/antisense pair, which can anneal to a complementary region thereon. The primed strand then becomes the point of origin for amplification. Amplification methods include, but are not limited to, thermal cycling and isothermal methods such as the polymerase chain reaction, recombinase polymerase amplification and rolling circle amplification; the last of these being applicable when $A_2$ is circularised. By any of these means, many amplicon copies of a region of $A_2$ and in some instances its sequence complement can be rapidly created. The exact methodologies for performing any of these amplification methods will be well-known to one of ordinary skill and the exact conditions and temperature regimes employed are readily available in the general literature to which the reader is directed. Specifically, in the case of the polymerase chain reaction (PCR), the methodology generally comprises extending the primer oligonucleotide against the $A_2$ strand in the 5'-3' direction using a polymerase and a source of the various single nucleoside triphosphates until a complementary strand is produced; dehybridising the double-stranded product produced to regenerate the $A_2$ strand and the complementary strand; re-priming the $A_2$ strand and any of its amplicons and thereafter repeating these extension/dehybridisation/repriming steps multiple times to build-up a concentration of $A_2$ amplicons to a level where they can be reliably detected.

In some embodiments, the first reaction mixture further comprises a ligation probe oligonucleotide C, and the partially digested strand $A_1$ is ligated at the 3' end to the 5' end of C, while in another embodiment, $A_1$ is circularised through ligation of its 3' and 5' ends;

in each case to create an oligonucleotide $A_2$.

In one embodiment, the ligation of $A_1$ occurs:

during step (a); or during step (b); or inbetween steps (a) and (b).

In one embodiment, $A_1$ is optionally extended in 5'-3' direction prior to ligation.

In some embodiments, this optional extension and the ligation are performed against the target oligonucleotide, while in another embodiment they are performed through addition of a further splint oligonucleotide D to which $A_1$ anneals prior to extension and/or ligation. In one embodiment, D comprises an oligonucleotide region complementary to the 3' end of $A_1$ and a region complementary to either the 5' end of oligonucleotide C or to the 5' end of $A_1$.

In another embodiment, D is unable to extend against $A_1$ by virtue of either a 3'-end modification or through a nucleotide mismatch between the 3' end of D and the corresponding region of $A_1$.

In some embodiments, the ligation probe C has a 5' region complementary to at least part of a 5' end region of a splint oligonucleotide D or to the target oligonucleotide. By such means, a second intermediate product is formed in which the $A_2$ strand is comprised of $A_1$, C and optionally an intermediate region formed by extension of $A_1$ in the 5'-3' direction to meet the 5' end of C. In such an embodiment, the primers employed in step (c) (see below) are chosen to amplify at least a region of $A_2$ including the site at which ligation of the $A_1$ to C has occurred. In this embodiment, we have found that it is advantageous to include a 3' blocking group on C so that a 3'-5' exonuclease can be used to digest any non-ligated $A_1$ prior to amplification. Suitable polymerases which may be used include but are not limited to Hemo KlenTaq, Mako and Stoffel Fragment.

In some embodiments, the first reaction mixture further comprises a phosphatase or phosphohydrolase to remove by hydrolysis the nucleoside triphosphates produced by the pyrophosphorolysis reaction thereby ensuring that the pyrophosphorolysis reaction can continue and does not become out-competed by the forward polymerisation reaction.

In some embodiments, prior to or during step (b) the products of the previous step are treated with a pyrophosphatase to hydrolyse the pyrophosphate ion, preventing further pyrophosphorolysis from occurring and favouring the forward polymerisation reaction.

In some embodiments, prior to or during step (b) the products of the previous step are treated with an exonuclease.

In some embodiments, the enzyme which performs pyrophosphorolysis of $A_0$ to form partially digested strand $A_1$ also amplifies $A_2$. The person skilled in the art will appreciate there exists many such enzymes.

The amplicons are detected and the information obtained are used to infer whether the polynucleotide target sequence is present or absent in the original analyte and/or a property associated therewith. For example, by this means a target sequence characteristic of a cancerous tumour cell may be detected with reference to specific SNPs being looked for. In another embodiment, a target sequence characteristic of the genome of a virus of bacterium (including new mutations thereof) may be detected. Many methods of detecting the amplicons or identification regions can be employed including for example an oligonucleotide binding dye, a sequence-specific molecular probe such as fluorescently-labelled molecular beacon or hairpin probe. Alternatively, direct sequencing of the $A_2$ amplicons can be performed using one of the direct sequencing methods employed or reported in the art. Where oligonucleotide binding dyes, fluorescently labelled beacons or probes are employed it is convenient to detect the amplicons using an arrangement comprising a source of stimulating electromagnetic radiation (laser, LED, lamp etc.) and a photodetector arranged to detect emitted fluorescent light and to generate therefrom a signal comprising a data stream which can be analysed by a microprocessor or a computer using specifically-designed algorithms.

In some embodiments, detection is achieved using one or more oligonucleotide fluorescent binding dyes or molecular probes. In such embodiments, an increase in signal over time resulting from the generation of amplicons of $A_2$ is used to infer the concentration of the target sequence in the analyte. In one embodiment that the final step of the method further comprises the steps of:
i. labelling the products of step (b) using one or more oligonucleotide fluorescent binding dyes or molecular probes;
ii. measuring the fluorescent signal of the products;
iii. exposing the products to a set of denaturing conditions; and
identifying the polynucleotide target sequence in the analyte by monitoring changes in the fluorescent signal of the products during exposure to the denaturing conditions.

In some embodiments, multiple probes $A_0$ are employed, each selective for a different target sequence and each including an identification region, and further characterised in that the amplicons of $A_2$ include this identification region and therefore the target sequences present in the analyte are inferred through the detection of the identification region(s). In such embodiments detection of the identification regions(s) is carried out using molecular probes or through sequencing.

In some embodiments, is the one or more nucleic acid analytes are split into multiple reaction volumes, each volume having a one or more probe oligonucleotide $A_0$, introduced to detect different target sequences.

In some embodiments, wherein different probes $A_0$ are used the different probes $A_0$ comprise one or more common priming sites, allowing a single or single set of primers to be used for amplification.

In another aspect of the invention, there is provided a method of identifying a target polynucleotide sequence in a given nucleic acid analyte characterised by the steps of any previous embodiment of the invention wherein the multiple copies of $A_2$, or a region of $A_2$, are labelled using one or more oligonucleotide fluorescent binding dyes or molecular probes. The fluorescent signal of these multiple copies is measured and the multiple copies are exposed to a set of denaturing conditions. The target polynucleotide sequence is the identified by monitoring a change in the fluorescent signal of the multiple copies during exposure to the denaturing conditions.

In some embodiments, the denaturing conditions may be provided by varying the temperature e.g. increasing the temperature to a point where the double strand begins to dissociate. Additionally or alternatively, the denaturing conditions may also be provided by varying the pH such that the conditions are acidic or alkaline, or by adding in additives or agents such as a strong acid or base, a concentrated inorganic salt or organic solvent e.g. alcohol.

In another aspect of the invention, there is provided the use of the methods described above to screen mammalian subjects, especially human patients, for the presence of infectious diseases, cancer or for the purpose of generating companion diagnostic information.

In a further aspect of the invention, there is provided control probes for use in the methods as described above. Embodiments of the current invention include those wherein the presence of a specific target sequence, or sequences, is elucidated by the generation of a fluorescent signal. In such embodiments, there may inevitably be a level of signal generated from non-target DNA present in the sample. For a given sample, this background signal has a later onset than the 'true' signal, but this onset may vary between samples. Accurate detection of the presence of low concentrations of target sequence, or sequences, thus relies on knowledge of what signal is expected in its absence. For contrived samples references are available, but for true 'blind' samples from patients this is not the case. The control probes ($E_0$) are utilised to determine the expected background signal profile for each assay probe. The control probe targets a sequence not expected to be present in the sample and the signal generated from this probe can then be used to infer the expected rate of signal generation from the sample in the absence of target sequence.

Thus there is provided a method of detecting a target polynucleotide sequence in a given nucleic acid analyte according to any of the previously described methods characterised by the steps of:
a. either subsequently or concurrently repeating the steps of the methods using a second single-stranded probe oligonucleotide $E_0$ having a 3' end region at least partially mismatched to the target sequence, either using a separate aliquot of the sample or in the same aliquot and using a second detection channel;
b. inferring the background signal expected to be generated from $A_0$ in the absence of any target analyte in the sample; and
c. through comparison of the expected background signal inferred in (a) with the actual signal observed in the presence of the target analyte inferring the presence or absence of the polynucleotide target sequence in the analyte.

In some embodiments, the control probe ($E_0$) and $A_0$ are added to separate portions of the sample while in another embodiment the $E_0$ and $A_0$ are added to the same portion of the sample and different detection channels (e.g. different colour dyes) used to measure their respective signals. The signal generated by $E_0$ may then be utilised to infer and correct for the background signal expected to be generated by $A_0$ in the absence of the polynucleotide target sequence in the sample. For example, a correction of the background signal may involve the subtraction of the signal observed from $E_0$ from that observed from $A_0$, or through the calibration of the signal observed from $A_0$ using a calibration curve of the relative signals generated by $A_0$ and $E_0$ under varying conditions.

In some embodiments, a single $E_0$ can be used to calibrate all of the assay probes which may be produced.

In some embodiments, a separate $E_0$ may be used to calibrate each amplicon of the sample DNA generated in an initial amplification step. Each amplicon may contain multiple mutations/target sequences of interest, but a single $E_0$ will be sufficient to calibrate all of the assay probes against a single amplicon.

In a further embodiment, a separate $E_0$ may be used for each target sequence. For example, if a C>T mutation is being targeted, an $E_0$ could be designed that targets a C>G mutation in the same site that is not known to occur in patients. The signal profile generated by $E_0$ under various conditions can be assessed in calibration reactions and these data used to infer the signal expected from the assay probe targeting the C>T variant when this variant is not present.

The specificity of the methods of the current invention may be improved by blocking at least a portion of wild-type DNA, promoting annealing of $A_0$ only to the target polynucleotide sequences. Blocking oligonucleotides can be used to improve the specificity of the polymerase chain reaction (PCR). The general technique used is to design an oligonucleotide that anneals between the PCR primers and is not able to be displaced or digested by the PCR polymerase. The oligonucleotide is designed to anneal to the non-target (usually healthy) sequence, while being mismatched (often by a single base) to the target (mutant) sequence. This mismatch results in a different melting temperature against the two sequences, the oligonucleotide being designed to remain annealed to the non-target sequence at the PCR extension temperature while dissociating from the target sequence.

The blocking oligonucleotides may often have modifications to prevent its digestion by the exonuclease activity of the PCR polymerase, or to enhance the melting temperature differential between the target and non-target sequence.

The incorporation of a locked nucleic acid (LNA) or other melting temperature altering modification into a blocking oligonucleotide can significantly increase the differential in melting temperature of the oligonucleotide against target and non-target sequences.

Thus there is provided an embodiment of the invention wherein blocking oligonucleotides are used. The blocking oligonucleotides must be resistant to the pyrophosphorolysing (PPL) reaction to ensure they are not digested or displaced. This can be achieved in a number of different ways, for example via mismatches at their 3' ends or through modifications such as phosphorothioate bonds or spacers.

In such embodiments or an aspect of the present invention where blocking oligonucleotides are used, the method of detecting a target polynucleotide sequence in a given nucleic acid analyte is characterised by annealing single-stranded blocking oligonucleotides to at least a subset of non-target polynucleotide sequences before, or during, the same step wherein the analyte target sequence is annealed to a single-stranded probe oligonucleotide $A_0$ to create a first intermediate product which is at least partially double-stranded and in which the 3' end of $A_0$ forms a double-stranded complex with the analyte target sequence.

In some embodiments, the blocking oligonucleotides are made to be resistant to the pyrophosphorolysing reaction via mismatches at their 3' ends. In another embodiment, the blocking oligonucleotides are made to be resistant via the presence of a 3'-blocking group. In another embodiment the blocking oligonucleotides are made to be resistant via the presence of spacers or other internal modifications. In a further embodiment the blocking oligonucleotides include both a melting temperature increasing modification or modified nucleotide base and are rendered resistant to pyrophosphorolysis.

References herein to 'phosphatase enzymes' refer to any enzymes, or functional fragments thereof, with the ability to remove by hydrolysis the nucleoside triphosphates produced by the methods of the current invention. This includes any enzymes, or functional fragments thereof, with the ability to cleave a phosphoric acid monoester into a phosphate ion and an alcohol.

References herein to 'pyrophosphatase enzymes' refer to any enzymes, or functional fragments thereof, with the ability to catalyse the conversion of one ion of pyrophosphate to two phosphate ions.

This also includes inorganic pyrophosphatases and inorganic diphosphatases. A non-limiting example is thermostable inorganic pyrophosphate (TIPP).

In some embodiments there is provided a modified version of any previously described embodiment wherein the use of a pyrophosphatase is optional.

In some embodiments of the invention there is provided a kit for use in a method of detecting a target polynucleotide sequence in a given nucleic acid analyte present in a sample, comprising:
(a) a single-stranded probe oligonucleotide $A_0$, capable of forming a first intermediate product with a target polynucleotide sequence, said intermediate product being at least partially double-stranded;
(b) a ligase;
(c) a pyrophosphorylising enzyme capable of digesting the first intermediate product in the 3'-5' direction from the end of $A_0$ to create a partially digested strand $A_1$;
(d) at least one single-stranded primer oligonucleotide that is substantially complementary to a portion of $A_0$;
(e) an amplification enzyme; and
(f) suitable buffers.

In one embodiment the kit further comprises a source of pyrophosphate ion.

Suitable source(s) of pyrophosphate ion are as described previously.

In some embodiments, the kit further comprises suitable positive and negative controls.

In some embodiments, the kit may further comprise one or more control probes ($E_0$) which are as previously described.

In some embodiments, the kit may further comprise one or more blocking oligonucleotides which are as previously described.

In some embodiments, the kit may further comprises one or more control probes ($E_0$) and one or more blocking oligonucleotides.

In some embodiments, the 5' end of $A_0$ may be rendered resistant to 5'-3' exonuclease digestion and the kit may further comprises a 5'-3' exonuclease.

In some embodiments a kit may further comprise a ligation probe oligonucleotide C.

In some embodiments a kit may further comprise a splint oligonucleotide D.

In some embodiments, a kit may comprise both C and D.

The ligation probe C may comprise a 3' or internal modification protecting it from 3'-5' exonuclease digestion.

D may comprise an oligonucleotide region complementary to the 3' end of $A_1$ and a region complementary to either the 5' end of oligonucleotide C or the 5' end of $A_1$.

In some embodiments, D may be unable to undergo extension against $A_1$ by virtue of either a 3' modification or through a mismatch between the 3' end of D and the corresponding region of $A_1$ or C.

In some embodiments, the kit may further comprise dNTPs, a polymerase and suitable buffers for the initial amplification of a target polynucleotide sequence present in a sample.

In some embodiments, the kit may further comprise a dUTP incorporating high fidelity polymerase, dUTPs and uracil-DNA N-glycosylase (UDG).

In some embodiments, the kit may further comprise a phosphatase or a phosphohydrolase.

In some embodiments, the kit may further comprise a pyrophosphatase. The pyrophosphatase may be hot start.

In some embodiments, the kit may further comprise a proteinase.

In some embodiments, the kit may further comprise one or more oligonucleotide binding dyes or molecular probes.

In some embodiments, the kit may further comprises multiple $A_0$, each selective for a different target sequence and each including an identification region.

In some embodiments, the amplification enzyme, of (e), and the pyrophosphorylising enzyme are the same.

The kit may further comprise purification devices and reagents for isolating and/or purifying a portion of polynucleotides, following treatment as described herein. Suitable reagents are well known in the art and include gel filtration columns and washing buffers.

In one embodiment of the invention there is provided a device comprising:

at least a fluid pathway between a first region, a second region and a third region, wherein the first region comprises one or more wells, wherein each well comprises:

dNTPs;

at least one single-stranded primer oligonucleotide; an amplification enzyme for the initial amplification of DNA present in a sample; and wherein the second region comprises one or more wells, wherein each well comprises:

a single-stranded probe oligonucleotide $A_0$, capable of forming a first intermediate product with a target polynucleotide sequence, said intermediate product being at least partially double-stranded;

a pyrophosphorylising enzyme capable of digesting the first intermediate product in the 3'-5' direction from the end of $A_0$ to create a partially digested strand $A_1$; and wherein the third region comprises one or more wells, wherein each well comprises:

dNTPs;

buffers;

an amplification enzyme;

a means for detecting a signal derived from $A_2$ or a portion thereof, or multiple copies of $A_2$ or multiple copies of a portion thereof; and wherein the wells of the second region or the wells of the third region further comprise at least one single-stranded primer oligonucleotide that is substantially complementary to a portion of $A_0$.

In some embodiments, the dNTPs of each well of the first region may be dUTP, dGTP, dATP and dCTP and each well may further comprise a dUTP incorporating high fidelity polymerase and uracil-DNA N-glycosylase (UDG).

In some embodiments, each well of the second region may further comprise a source of pyrophosphate ion.

In some embodiments, the 5' end of $A_0$ may be rendered resistant to 5'-3' exonuclease digestion and the wells of the second region may further comprises a 5'-3' exonuclease.

In some embodiments, each well of the second or third regions may further comprise a ligase and a ligation probe oligonucleotide C or a splint oligonucleotide D.

The ligation probe C may comprise a 3' or internal modification protecting it from 3'-5' exonuclease digestion.

The splint oligonucleotide D may comprise an oligonucleotide region complementary to the 3' end of $A_1$ and a region complementary to either the 5' end of oligonucleotide C or to the 5' end of $A_1$.

D may be unable to undergo extension against $A_1$ by virtue of either a 3' modification or through a mismatch between the 3' end of D and the corresponding region of $A_1$ or C.

In some embodiments, the dNTPs may be hot start and each well of the second region may further comprise a phosphatase or a phosphohydrolase.

In some embodiments, each well of the second region may further comprise a pyrophosphatase.

In some embodiments, the pyrophosphatase may be a hot start.

In some embodiments, each well of the third region may further comprise one or more oligonucleotide binding dyes or molecular probes.

In some embodiments, each well of the second region may comprise at least one or more different $A_0$ that is selective for a target sequence including an identification region.

In some embodiments, the amplification enzyme and the pyrophosphorylising enzyme in the second region may be the same.

In some embodiments, there may be a fourth region comprising one or more wells, wherein each well may comprise a proteinase and wherein said fourth region may be located between the first and second regions.

In some embodiments, the second and third regions of the device may be combined such that the wells of the second region further comprise:

dNTPs;

buffers;

an amplification enzyme; and a means for detecting a signal derived from $A_1$ or a portion thereof, or multiple copies of $A_1$ or multiple copies of a portion thereof.

In some embodiments, the first region may be fluidically connected to a sample container via a fluidic interface.

In some embodiments, heating and/or cooling elements may be present at one or more regions of the device.

In some embodiments, heating and/or cooling may be applied to one or more regions of the device.

In some embodiments, each region of the device may independently comprise at least 100 or 200 wells.

In some embodiments, each region of the device may independently comprise between about 100 and 300, 400, 500, 600, 700, 800, 900, 1000, 1100, 1200, 1300, 1400, 1500 or more wells. The wells may be of any shape and their locations may be arranged in any format or pattern on a substrate.

In some embodiments, the well-substrate can be constructed from a metal (e.g. gold, platinum, or nickel alloy as non-limiting examples), ceramic, glass, or other PCR compatible polymer material, or a composite material. The well-substrate includes a plurality of wells.

In some embodiments, the wells may be formed in a well-substrate as blind-holes or through-holes. The wells may be created within a well-substrate, for example, by laser drilling (e.g. excimer or solid-state laser), ultrasonic embossing, hot embossing lithography, electroforming a nickel mold, injection molding, and injection compression molding.

In some embodiments, individual well volume may range from 0.1 to 1500 nl. In one embodiment, 0.5 to 50 nL. Each well may have a volume of about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, or 500 nL.

In some embodiments, well dimensions may have any shape, for example, circular, elliptical, square, rectangular, ovoid, hexagonal, octagonal, conical, and other shapes well known to persons of skill in the art.

In some embodiments, well shapes may have cross-sectional areas that vary along an axis. For example, a square hole may taper from a first size to a second size that is a fraction of the first size.

In some embodiments, well dimensions may be square with diameters and depths being approximately equal.

In some embodiments, walls that define the wells may be non-parallel.

In some embodiments, walls that define the wells may converge to a point. Well dimensions can be derived from the total volume capacity of the well-substrate.

In some embodiments, well depths may range from 25 μm to 1000 μm.

In one embodiment, wells may have a depth of 25, 50, 75, 100, 150, 200, 250, 300, 350, 400, 450, 500, 550, 600, 650, 700, 750, 800, 850, 900, 950 or 1000 µm.

In some embodiments, well diameter may range from about 25 µm about 500 µm. In some embodiments, wells may have a width of 25, 50, 75, 100, 125, 150, 175, 200, 225, 250, 275, 300, 325, 350, 375, 400, 425, 450, 475 or 500 µm.

In some embodiments, portions of one or more regions of the device may be modified to encourage or discourage fluid adhered. Surfaces defining the wells may be coated with a hydrophilic material (or modified to be hydrophilic), and thus encourage retention of fluid.

In some embodiments, portions of one or more regions of the device, may be coated with a hydrophobic material (or modified to be hydrophobic) and thus discourage retention of fluid thereon. The person skilled in the art will understand that other surface treatments may be performed such that fluid is preferably held within the wells, but not on upper surfaces so as to encourage draining of excess fluid.

In some embodiments, the wells of the well-substrate may be patterned to have a simple geometric pattern of aligned rows and columns, or patterns arranged diagonally or hexagonally. In one embodiment, the wells of the well-substrate may be patterned to have complex geometric patterns, such as chaotic patterns or isogeometric design patterns.

In some embodiments, the wells may be geometrically separated from one another and/or feature large depth to width ratios to help prevent cross-contamination of reagents.

In some embodiments, the device may comprise one or more axillary regions which are usable to provide process fluids, such as oil or other chemical solutions to one or more of the regions of the device. Such auxiliary regions may be fluidically connected to one or more of the regions of the device via one or more membranes, valves and/or pressure severable substrates (i.e. materials that break when subjected to a pre-determined amount of pressure from fluid within an auxiliary region or adjacent portion of the fluid pathway) such as metal foil or thin film.

In some embodiments, the fluid pathway of the device may include extensive torturous portions. A torturous path between the inlet passage of the fluid pathway and one or more of the regions of the device can be helpful for control and handling of fluid processes. A torturous path can help reduce formation of gas bubbles that can interfere with flowing oil through the fluid pathway.

In some embodiments, the device may further comprises a gas permeable membrane which enables gas to be evacuated from the wells of one or more regions of the device, while not allowing fluid to pass through. The gas permeable membrane may be adhered to the well-substrate of the device by a gas permeable adhesive. In one embodiment, the membrane may be constructed from polydimethylsiloxane (PDMS), and has a thickness ranging from 20-1000 µm. In some embodiments the membrane may have a thickness ranging from 100-200 µm.

In some embodiments, all or portions of the well-substrate may contain conductive metal portions (e.g., gold) to enable heat transfer from the metal to the wells. In one embodiment, the interior surfaces of wells may be coated with a metal to enable heat transfer.

In some embodiments, after appropriate reagents have filled the wells of one or more regions of the device, an isolation oil or thermally conductive liquid may be applied to the device to prevent cross-talk.

In some embodiments, the wells of one or more regions of the device may be shaped to taper from a large diameter to a smaller diameter, similar to a cone. Cone-shaped wells with sloped walls enables the use of a non-contact deposition method for reagents (e.g., ink jet). The conical shape also aids in drying and has been found to prevent bubbles and leaks when a gas permeable membrane is present.

In some embodiments, the wells of one or more regions of the device may be filled by advancing a sample fluid (e.g. via pressure) along the fluid pathway of the device. As the fluid passes over the wells of one or more regions of the device, each well becomes filled with fluid, which is primarily retained within the wells via surface tension. As previously described, portions of the well-substrate of the device may be coated with a hydrophilic/hydrophobic substance as desired to encourage complete and uniform filing of the wells as the sample fluid passes over.

In some embodiments, the wells of one or more regions of the device may be 'capped' with oil following filling. This can then aid in reducing evaporation when the well-substrate is subjected to heat cycling. In one embodiment, following oil capping, an aqueous solution can fill one or more regions of the device to improve thermal conductivity.

In some embodiments, the stationary aqueous solution may be pressurised within one or more regions of the device to halt the movement of fluid and any bubbles.

In some embodiments, oil such as mineral oil may be used for the isolation of the wells of one or more regions of the device and to provide thermal conductivity. However, any thermal conductive liquid, such as fluorinated liquids (e.g., 3M FC-40) can be used. References to oil in this disclosure should be understood to include such alternatives as the skilled person in the art will appreciate are applicable.

In some embodiments, the device may further comprise one or more sensor assemblies.

In some embodiments, the one or more sensor assemblies may comprise a charge coupled device (CCD)/complementary metal-oxide-semiconductor (CMOS) detector coupled to a fiber optic face plate (FOFP). A filter may be layered on top of the FOPF, and placed against or adjacent to the well-substrate. In one embodiment, the filter can be layered (bonded) directly on top of the CCD with the FOPF placed on top.

In some embodiments, a hydration fluid, such as distilled water, may be heated within the first region or one of the auxiliary regions such that one or more regions of the device has up to 100% humidity, or at least sufficient humidity to prevent over evaporation during thermal cycling.

In some embodiments, after filing of the device is complete, the well-substrate may be heated by an external device that is in thermal contact with the device to perform thermal cycling for PCR.

In some embodiments, non-contact methods of heating may be employed, such as RFID, Curie point, inductive or microwave heating. These and other non-contact methods of heating will be well known to the person skilled in the art. During thermal cycling, the device may be monitored for chemical reactions via the sensor arrangements previously described.

In some embodiments, reagents that are deposited in one or more of the wells of one or more of the regions of the device are deposited in a pre-determined arrangement.

In some embodiments there is provided a method comprising:

providing a sample fluid to a fluid pathway of a device wherein the device comprises at least a fluid pathway between a first region, a second region and a third region, wherein the first, second and third regions independently comprise one or more wells;

filling the second region with the amplified fluid from the first region such that one or more wells of the second region is coated with the amplified fluid;

evacuating the amplified fluid from the second region such that one or more wells remain wetted with at least some of the amplified fluid;

filling the third region with the fluid evacuated from the second region such that one or more wells of the third region is coated with this fluid; and evacuating the fluid from the third chamber such that the one or more wells remains wetted with at least some of this fluid.

In some embodiments of the method, the fluid pathway may be valve less.

In some embodiments of the method, the evacuated second region may be filled with a hydrophobic substance.

In some embodiments of the method, the evacuated third region may be filled with a hydrophobic substance.

In some embodiments of the method, the hydrophobic substance may be supplied from an oil chamber that is in fluid communication with the second and third regions.

In some embodiments of the method, the sample fluid may be routed along the fluid pathway in a serpentine manner.

In some embodiments, the method may further comprise applying heating and cooling cycles to the one or more of the first, second or third regions.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

It will further be appreciated by those skilled in the art that although the invention has been described by way of example with reference to several embodiments, it is not limited to the disclosed embodiments and that alternative embodiments could be constructed without departing from the scope of the invention as defined in the appended claims.

EXAMPLE 1

Simplified Protocols

For the purpose of this, and following sections, embodiments of the invention are exemplified and referred to as Protocol 1-5 respectively.

FIG. 1 provides an overview of the different Protocols.

Table 1 below shows an overview of the time taken to perform each Protocol:

TABLE 1

| Protocol | Time [min] | | | | |
|---|---|---|---|---|---|
| Step | 1 | 2 | 3 | 4 | 5 |
| PCR | | | 60-100 | | |
| Exo 5-3' | | 30 | | | — |
| Proteinase K | | 70 | | 15 | — |
| PPL | 30 | 30 | 30 | | 15 |
| Ligation | 20 | 20 | | | |
| TIPP | 10 | | 10 | | 50* |

TABLE 1-continued

| Protocol | Time [min] | | | | |
|---|---|---|---|---|---|
| Step | 1 | 2 | 3 | 4 | 5 |
| Exo | 10 | 10 | | | |
| RCA | | 50 | | | |
| Total time | 280-320 | 270-310 | 165-205 | 140-180 | 125-165 |

Tables 2 and 3 below show an overview of the enzymes used in each Protocol:

TABLE 2

| Protocol | Enzyme | | | | |
|---|---|---|---|---|---|
| Step | 1 | 2 | 3 | 4 | 5 |
| PCR | High Fidelity Polymerase, Uracil-DNA Glycosylase | | | | |
| Exo | 5-->3' Exonuclease | | | | — |
| Proteinase | Proteinase | | | | — |
| PPL | Pplase, diphosphatase | | Pplase, Ligase, 5-->3' exo, | | |
| Ligation | Ligase | Ligase, | diphosphatase | | |
| TIPP | Pyrophosphatase | Pyrophos- | Exonuclease | Pyrophos- | |
| Exo | Exonuclase | phatase | 3-->5' or/and | phatase, | |
| | 3-->5' or/and | | 5-->3', | DNA | |
| | 5-->3' | | Pyrophosphatase | polymerase | |
| Amplification | DNA polymerase | | | | |
| Number of enzymes | 12 | 12 | 10 | 9 | 8 |

TABLE 3

| Protocol | Enzyme | | | | |
|---|---|---|---|---|---|
| Step | 1 | 2 | 3 | 4 | 5 |
| PCR | PhusionU/Q5, UDG | | | | |
| Exo 5-3' | Lambda, PNK | | | | — |
| Proteinase K | Proteinase K | | | | |
| PPL | Mako/Klenow/BST | | Mako/Klenow/ | | |
| | L.F./Bsu, Apyrase | | BSTL. F./Bsu, | | |
| Ligation | E.coli Ligase/T 4 Ligase/T 3 Ligase/ HiFi Ligase/ 9oN Ligase | E.coli Ligase/T 4 Ligase/T 3 Ligase/ HiFi Ligase/ 9oN Ligase, TIPP | E.coli Ligase/T4 Ligase/T3 Ligase/ HiFi Ligase/ 9oN Ligase, Lambda exo, Apyrase | | |
| TIPP | TIPP | | ExoIII, TIPP | TIPP, BST L.F/BST 2.0 WS/Klenow/ phi29/AmpliTaq/ TaqPolymerase/ Q5/PhusionFlex | |
| Exo Amplification | T5, Exo III BST L.F./BST 2.0 WS/Klenow/phi29 | | | | |
| Number of enzymes | 12 | 12 | 10 | 9 | 8 |

Figure 2:
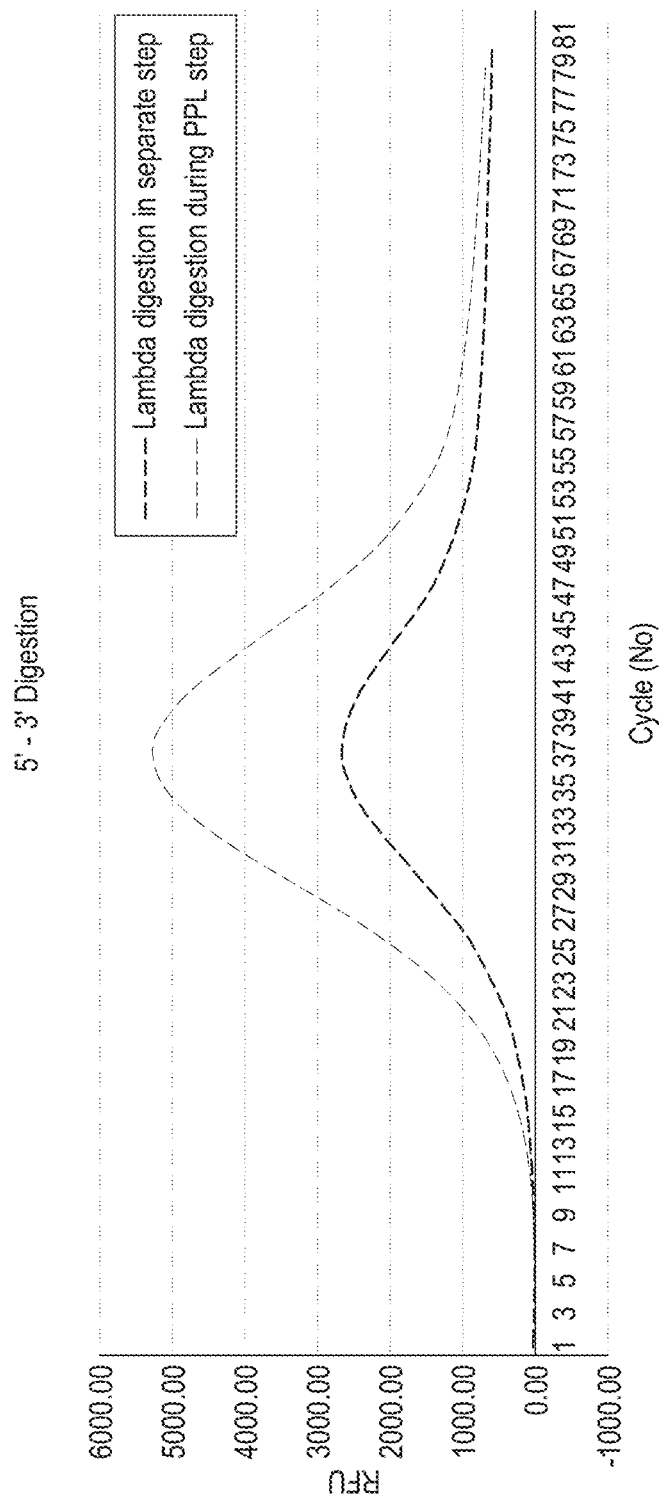
FIG. 2: A graph comparing the level of fluorescence detected (representing the presence of a particular target analyte sequence) when the 5'-3' exonuclease digestion step happens during the pre-amplification step and when it is moved to the pyrophosphorolysis/ligation step of the protocol (as in protocols 3-5). In this example, the 5'-3' exonuclease is Lambda.

As can be seen, the inventors have reduced total number of enzymes needed thus reducing the cost and complexity of the method. Surprisingly, the inventors discovered that moving the 5'-3' exonuclease addition from the pre-amplification step to the pyrophosphorolysis/ligation step of the protocol (as in protocols 3-5) results in a higher fluorescent signal (representing detection of particular target analyte sequence) as shown in FIG. 2.

EXAMPLE 2

Pyrophosphorylising (PPL) Enzymes

Figure 3A:
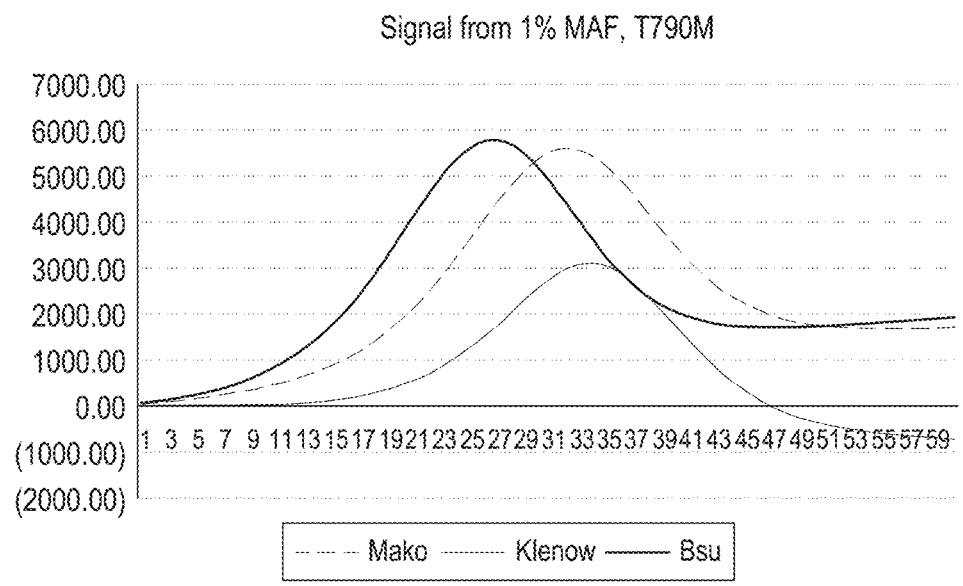
FIGS. 3(A)-3(B): The inventors have tested the method of Protocol 3 of the current invention using a range of different PPL enzymes.
Figure 3B:
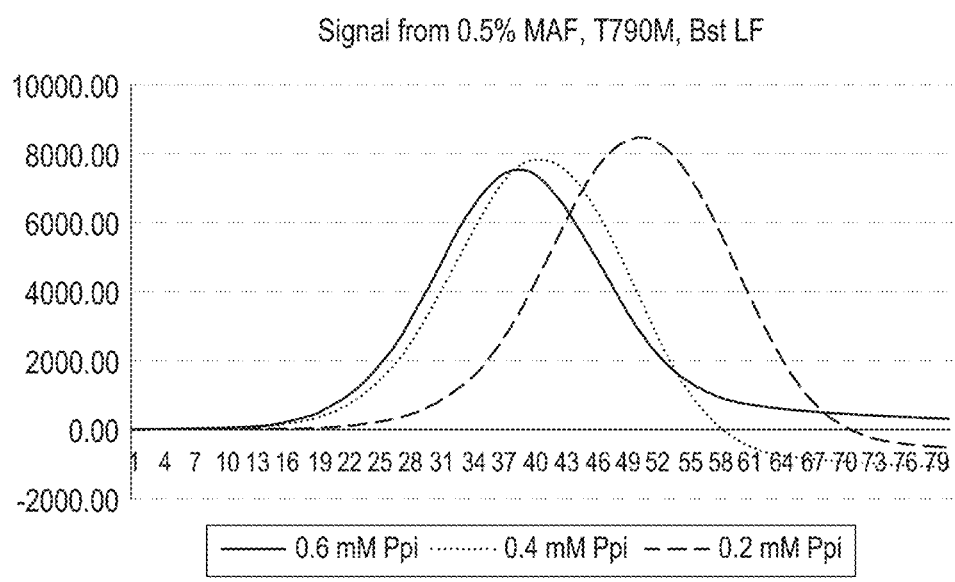

The inventors have tested the method of Protocol 3 of the current invention using a range of different PPL enzymes, the results of which can be seen in FIGS. 3(A)-3(B) FIG. 3(A) shows detection of 1% MAF T790M using Mako, Klenow and Bsu. FIG. 3(B) shows the detection of 0.5% MAF T790M using Bst LF at a range of different PPi concentrations.

The inventors have tested the method of Protocol 4 of the current invention using a range of different PPL enzymes, the results of which can be seen in FIGS. 4(A)-4(D).

EXAMPLE 3

Protocol 1 vs Protocol 4

Figure 5:
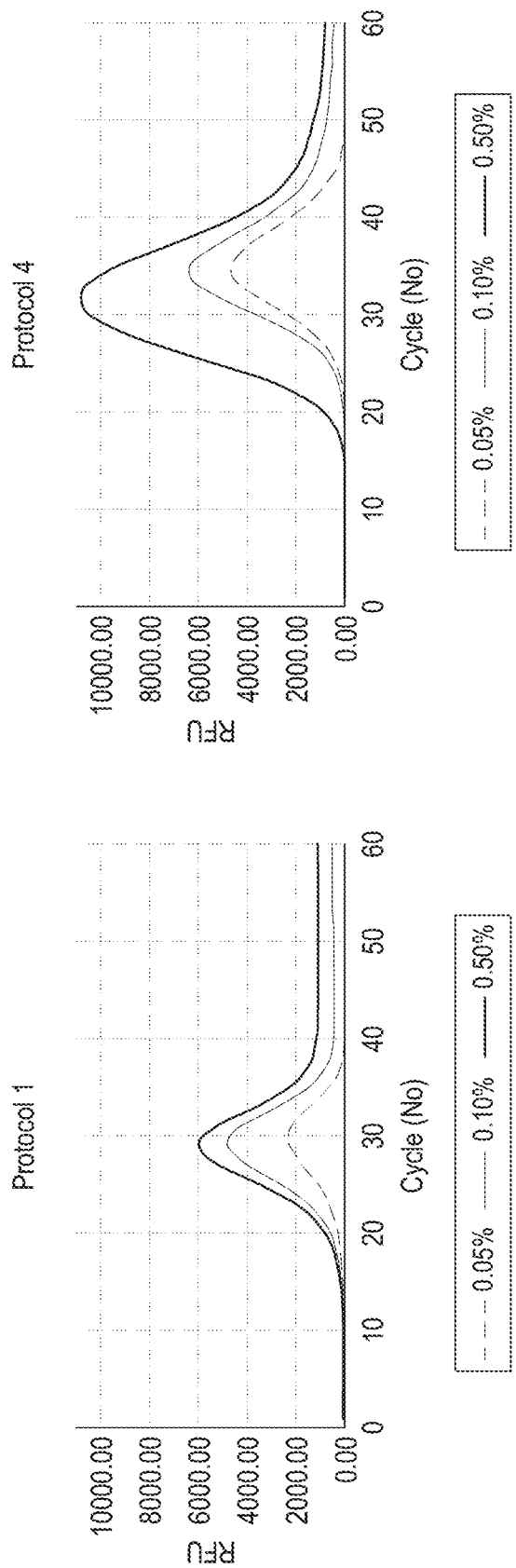
FIG. 5: Graphs showing the level of fluorescence detected (representing the presence of particular target analyte sequence) of 0.5%, 0.10% and 0.05% MAF Exon19 del_6223 detected according to Protocol 1 and Protocol 4.

The inventors have detected Exon19 del_6223 at 0.5%, 0.10% and 0.05% MAF, which can be seen in FIG. 5, using both Protocol 1 and Protocol 4. As can be seen, the fluorescent peaks are greater when using Protocol 4.

EXAMPLE 4

Protocol 4—Sensitivity

Figure 6:
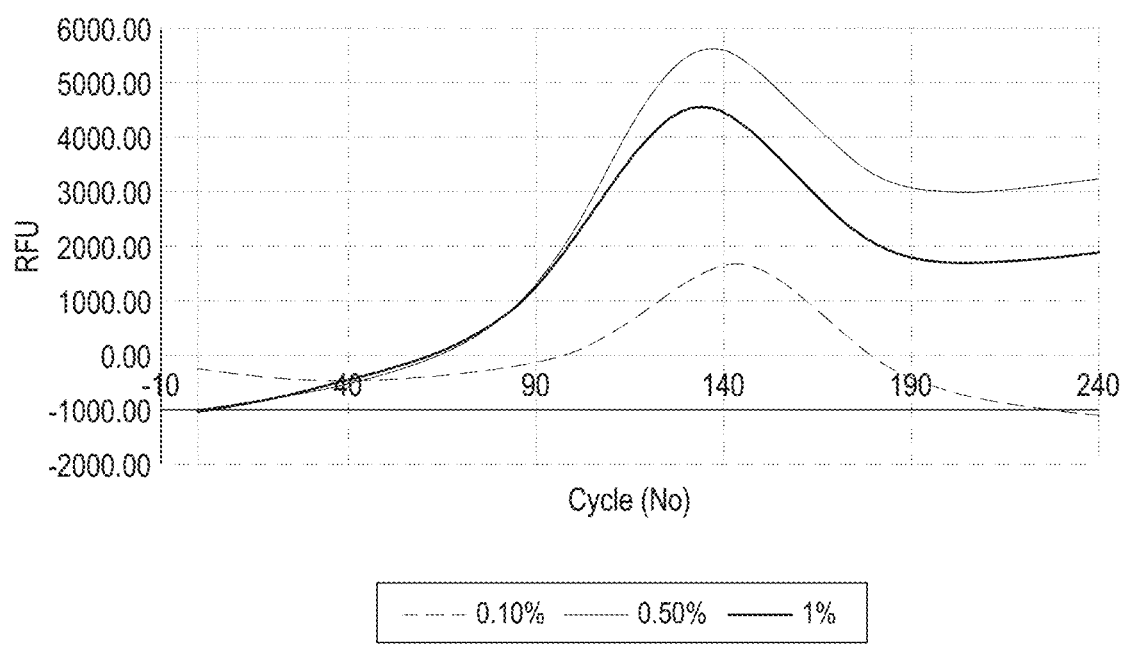
FIG. 6: The inventors have detected EGFR exon 20 T790M at 0.10%, 0.50% and 1% MAF according to Protocol 4.

The inventors have detected EGFR exon 20 T790M mutations at 0.10%, 0.50% and 1% MAF as shown in FIG. 6 according to Protocol 4.

EXAMPLE 5

Protocol 4—Is an Exonuclease Digestion Step Needed during RCA?

Figure 7:
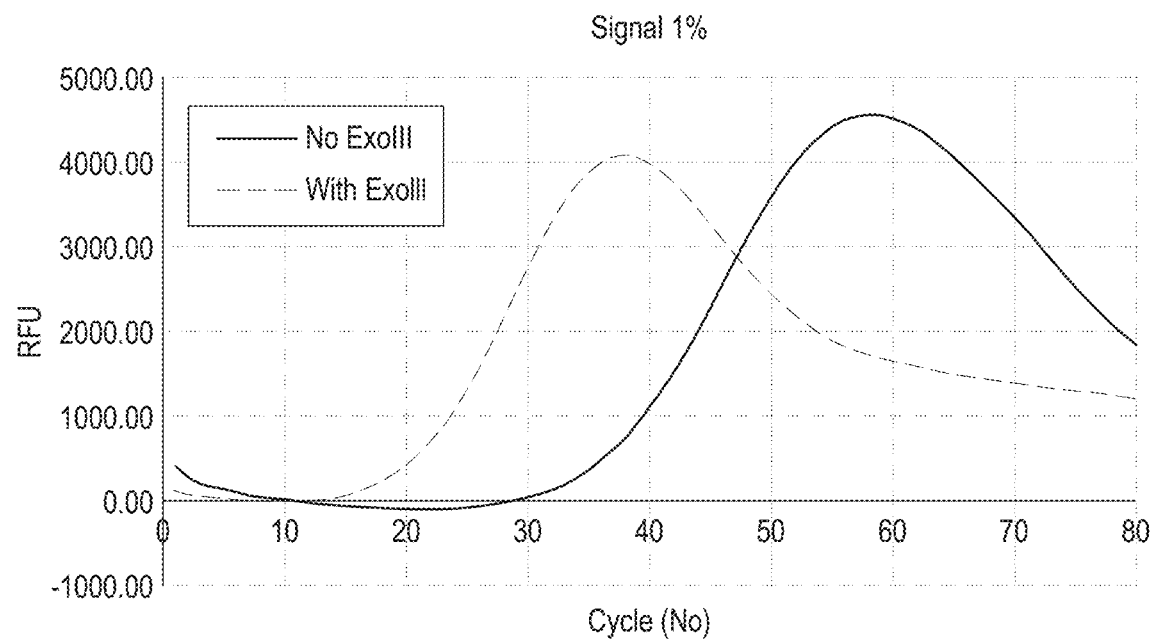
FIG. 7: shows detection of EGFR exon 20 T790M at 1% MAF with and without the presence of an exonuclease in the RCA step.

The inventors have demonstrated that an exonuclease digestion step during RCA is not essential. However, a detectable signal is detected later in the RCA if the exonuclease digestion step is omitted. FIG. 7 shows detection of EGFR exon 20 T790M at 1% MAF with and without the presence of an exonuclease in the RCA step.

EXAMPLE 6

Protocol 4—PPL:RCA Mix Ratio

Figure 8:
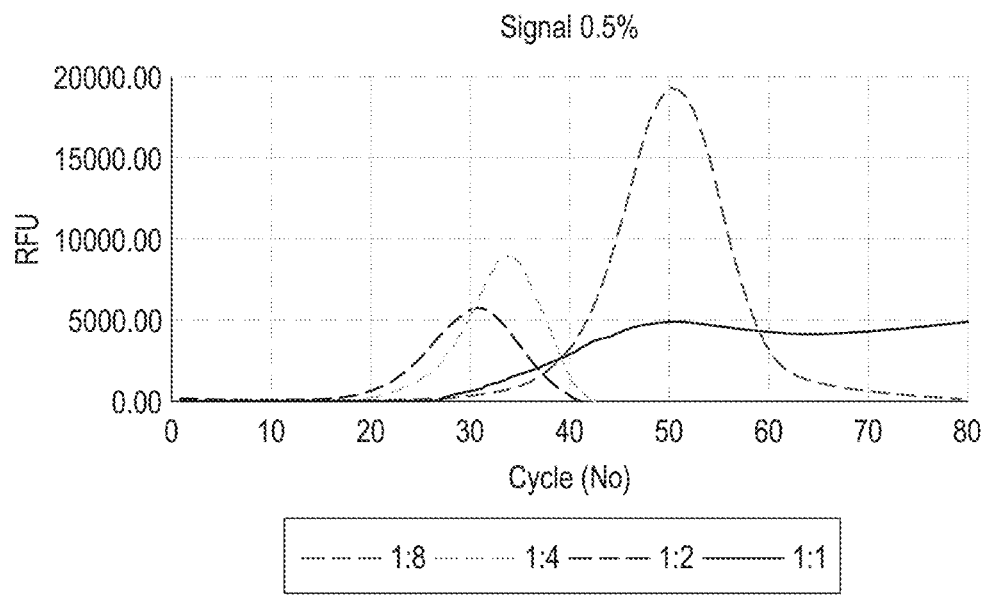
FIG. 8: The inventors have investigated what effect the PPL:RCA mix ratio has on the intensity of signal detected for 0.5% MAF EGFR exon 20 T790M, the results of which are shown in FIG. 8. As can be seen a ratio of 1:2 PPL:RCA mix results in the lowest signal intensity but at the earliest time point. This is followed closely in time by 1:4 PPL:RCA mix which has a greater signal intensity. The largest signal intensity is seen for 1:8 PPL:RCA mix at the latest time point in the reaction.

The inventors have investigated what effect the PPL:RCA mix ratio has on the intensity of signal detected for 0.5% MAF EGFR exon 20 T790M, the results of which are shown in FIG. 8. As can be seen a ratio of 1:2 PPL:RCA mix results in the lowest signal intensity but at the earliest time point. This is followed closely in time by 1:4 PPL:RCA mix which has a greater signal intensity. The largest signal intensity is seen for 1:8 PPL:RCA mix at the latest time point in the reaction.

EXAMPLE 7

Protocol 4—Dye Choice

Figure 9:
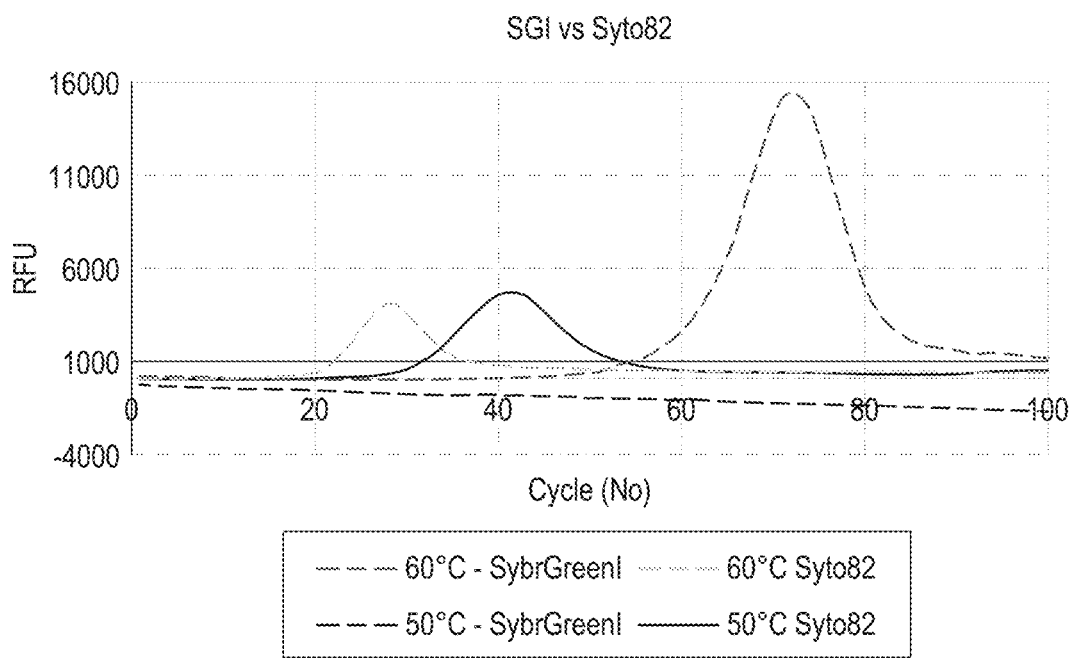
FIG. 9: shows the results of comparison experiments performed according to Protocol 4 using SybrGreenI (50° C. and 60° C.) and Syto82 (50° C. and 60° C.).

The inventors have investigated whether the dye used during RCA can be optimised. FIG. 9 shows the results of comparison experiments performed according to Protocol 4 using SybrGreenI (50° C. and 60° C.) and Syto82 (50° C. and 60° C.). The Syto82 dye allows the RCA to be run at a lower temperature of 50° C., whereas SybrGreenI requires the higher 60° C. temperature. A lower RCA temperature is needed for Protocol 5 which removes the addition of Proteinase K to the reaction mixture. The amplification enzyme used for preparing at least one single-stranded analyte of a nucleic acid comprised of a target polynucleotide region, for detection using the methods of the current invention, requires a temperature of greater than 50° C. to work. The use of SybrGreenI necessitates a reaction temperature of 60° C. and thus Proteinase K must be added at some point during the method to deactivate the amplification enzyme prior to RCA.

A lower RCA temperature may allow the methods of the invention to be carried out in a plate reader instead of qPCR.

The reaction utilising Syto82 is faster, as can be seen in FIG. 9, and although the total amount of fluorescence is lower for Syto82—this can be alleviated by the use of a higher concentration of Syto82 dye.

EXAMPLE 8

Protocol 4—BST L.F. vs BST 2.0 WS

Figure 10:
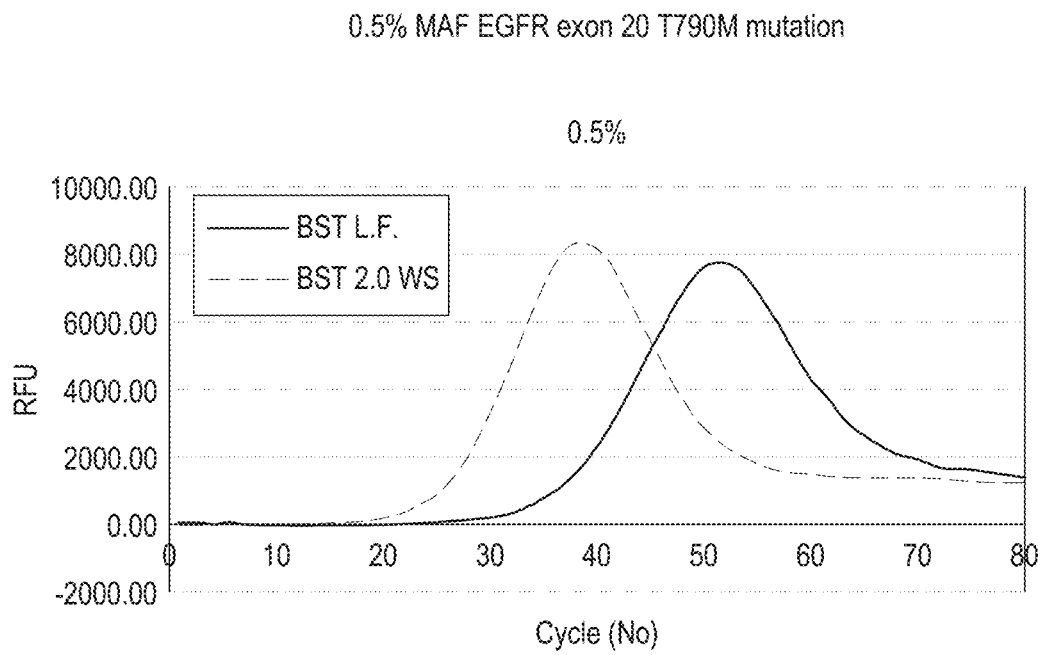
FIG. 10: The inventors have investigated the use of two different enzymes, BST L.F and BST 2.0 WS, for RCA according to Protocol 4.

The inventors have investigated the use of two different enzymes, BST L.F and BST 2.0 WS, for RCA according to Protocol 4 to detect 0.5% MAF EGFR exon 20 T790M mutation. The results of this are shown in FIG. 10 where it can be seen that the reaction is fastest with BST 2.0 WS. BST 2.0 WS is designed to incorporate dUTP, which helps with the speed of the reaction. There is a neglible difference in total signal intensity achieved between BST L.F. and BST 2.0 WS. According to its description, provided by New England Biolabs (NEB), BST 2.0 WS should be more stable and active only above 45° C.

EXAMPLE 9

Effect of PPL Enzymes on Signal Detection

Figures 11A, 11B:
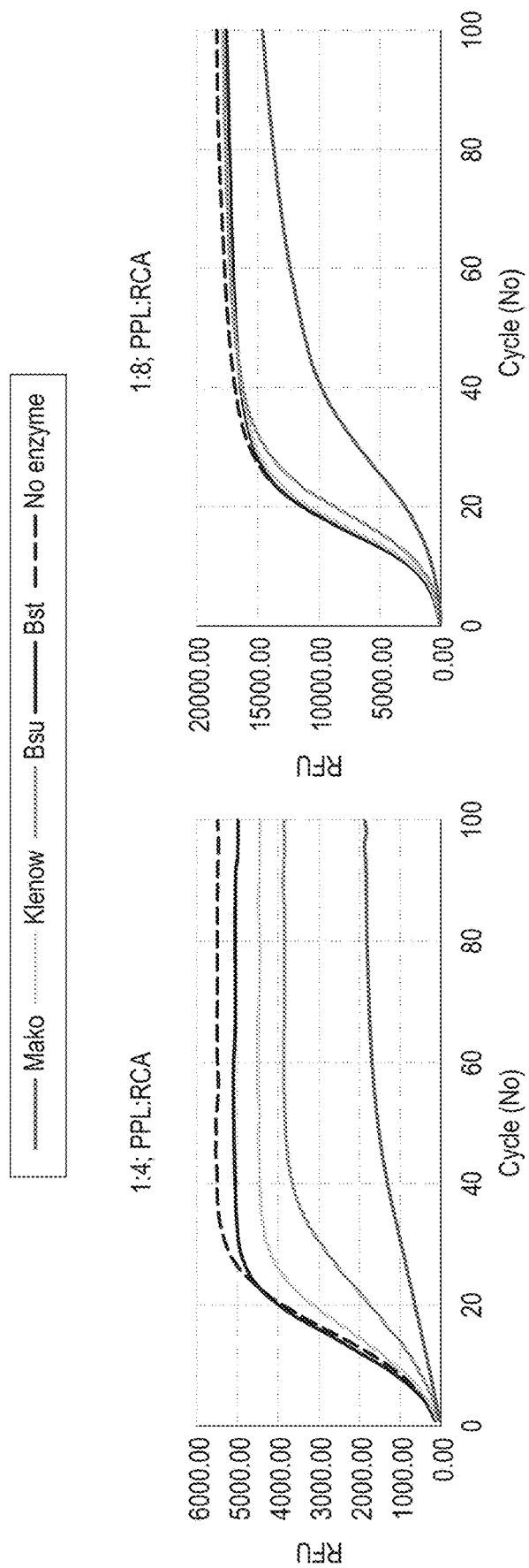
FIGS. 11(A)-11(B): The inventors have investigated the effect of different PPL enzymes on the RCA reaction at different PPL:RCA reaction mixture ratios. The results of which can be seen in FIG. 11(A) 1:4 PPL:RCA and FIG. 11(B) 1:8 PPL:RCA. All PPL enzymes impact the RCA reaction at 1:4 PPL:RCA ratio other than BST L.F. At 1:8 PPL:RCA ratio, all enzymes apart from BST L.F and Klenow impact the RCA reaction.

The inventors have investigated the effect of different PPL enzymes on the RCA reaction at different PPL:RCA reaction mixture ratios. The results of which can be seen in FIG. 11(A) 1:4 PPL:RCA and FIG. 11(B) 1:8 PPL:RCA. All PPL enzymes, excepting BST, impact the RCA reaction at 1:4 PPL:RCA ration. At 1:8 PPL:RCA ratio, BST and Klenow have no impact on the RCA reaction.

EXAMPLE 10

Pyrophosphorolysis, Ligation Specificity Against Single Nucleotide Mismatches A single-stranded first oligonucleotide 1 (SEQ ID NO 1) was prepared, having the following nucleotide sequence:

5'-/5Phos/A*T*G*TTCGATGAGCTTTGACAATACTTGAAGCTCGCAG

ATATAGGATGTTGCGATAGTCCAGGAGGCTGC-3'

A at position 1 has a 5' phosphate. Further, A (position 1), T (position 2), G (position 3) and T (position 4) are all linked with phosphorothioate bonds.

A single-stranded ligating oligonucleotide 2 (SEQ ID NO 2) was prepared, having the following nucleotide sequence:

5'- TGTCAAAGCTCATCGAACATCCTGGACTATGTCTCC-3' wherein A, C, G, and T represent nucleotides bearing the relevant characteristic nucleobase of DNA,
/5Phos/represent 5' end phosphate
* represent phosphorothioate bond A set of single-stranded oligonucleotides 3-4 (SEQ ID NOs 3-4) was also prepared, having the following nucleotide sequences in the 5' to 3' direction:

3:
TGCTGGGCATCTGCCTCACCTCCACCGTGCAGCTCATCACGCAGCTCATG

CCCTTCGGCAGCCTCCTGGACTATG

4:
TGCTGGGCATCTGCCTCACCTCCACCGTGCAGCTCATCACGCAGCTCATG

CCCTTCGGCTGCCTCCTGGACTATG wherein oligonucleotide 3 includes a 17 base region complementary to the 17 bases at the 3' end of oligonucleotide 1 and oligonucleotide 4 include the same region with single nucleotide mismatches at positions 3.

A first reaction mixture was then prepared, having a composition corresponding to that derived from the following formulation:
  0.5 uL 20× buffer pH 7.0
  0.25 uL 5× buffer pH 8.0
  0.25 uL 5× HF buffer
  0.2 uL oligonucleotide 1, 1000 nM
  0.3 uL oligonucleotide 2, 1000 nM
  1 uL oligonucleotide 2 (500 nM) or mixture of oligo 2 and 3 (500 and 0.5 nM respectively),
  0.3 U Klenow Fragment exo-(NEB)
  0.01 uL inorganic pyrophosphate, 10 mM
  0.0132 U Apyrase (ex. NEB)
  1 U E. coli DNA Ligase (ex. NEB)
  Water to 10 uL
wherein the 20× buffer comprised the following mixture:
  200 uL Tris Acetate, 1M, pH 7.0
  342.5 uL aqueous Magnesium Acetate, 1M
  120 uL aqueous Potassium Acetate, 5M
  50 uL Triton X-100 surfactant (10%)
  Water to 1 mL
wherein the 5× buffer comprised the following mixture:
  50 uL Trizma Acetate, 1M, pH 8.0
  25 uL aqueous Magnesium Acetate, 1M
  25 uL aqueous Potassium Acetate, 5M
  50 uL Triton X-100 surfactant (10%)
  Water to 1 mL Pyrophosphorolysis, followed by circularisation, via ligation of, oligonucleotide 1 was then carried out by incubating the mixture at 45° C. for 15 minutes and the resulting product mixture was used in the amplification reaction (Example 11).

EXAMPLE 11

Amplification of Circularised Probe

A pair of single stranded oligonucleotide primers 1 (SEQ ID NO 5) and 2 (SEQ ID NO 6) were prepared, having the following nucleotide sequences:

1: TCGCAACATCCTATATCTGC

2: TGAGCTTTGACAATACTTGA wherein A, C, G, and T represent nucleotides bearing the relevant characteristic nucleobase of DNA.

Figure 12:
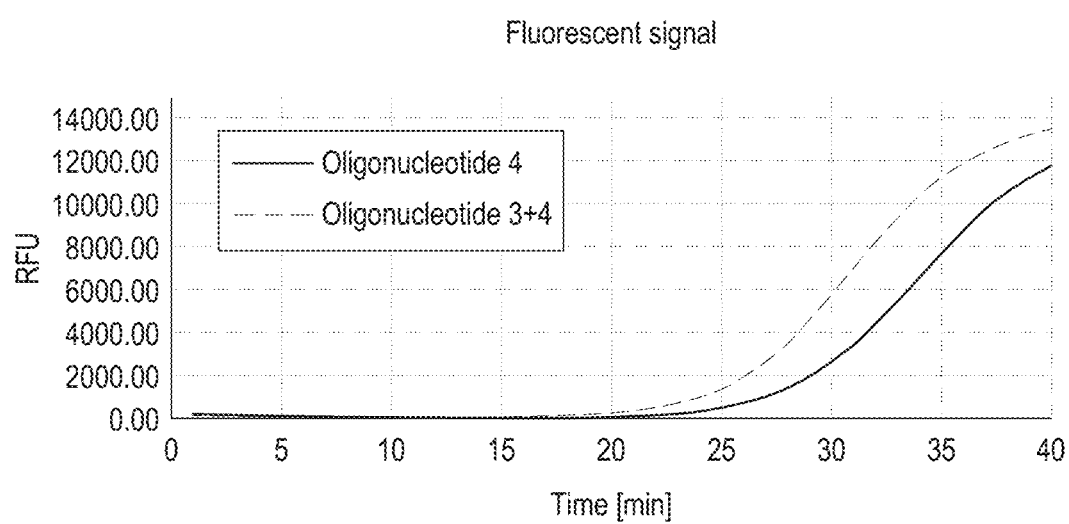
FIG. 12: Fluorescence measurement results for Example 11 showing that when oligonucleotide 3 and 4 are both present, the fluorescent signal appears faster in the reaction, showing that pyrophosphorolysis and ligation of oligonucleotide 3 has occurred in the first reaction mixture.

A second reaction mixture was then prepared, having a composition corresponding to that derived from the following formulation:
  3 uL 10× Thermopol buffer
  3.2 U BST 2.0 WS
  0.32 uL oligonucleotide 1, 10 uM
  0.32 uL oligonucleotide 2, 10 uM
  1.125 uL Syto82, 30 uM
  0.165 U Inorganic Pyrophosphatase
  1.2 uL dNTPs mix, 10 mM
  1.25 uL reaction mixture in Example 10
  Water to 11.25 uL
wherein the 10× Thermopol buffer comprised the following mixture:
  200 uL Tris—HCl pH=8.8, 1M
  100 uL NH4)2SO4, 1M
  100 uL mM KCl, 1M
  20 mM MgSO4, 1M
  10 uL Triton® X-100, 10%
  Water to 1 mL The reaction mix was then incubated at 50° C. for 40 minute and the resulting reaction product was then analysed by real-time fluorescence. The results of which are shown in FIG. 12. From this analysis it can be seen that when oligonucleotide 3 and 4 are both present, the fluorescent signal appears faster in the reaction, showing that pyrophosphorolysis and ligation of oligonucleotide 3 has occurred in the first reaction mixture.

The invention claimed is:

1. A method of detecting a target polynucleotide sequence in a nucleic acid analyte present in a sample, the method comprising the steps of:
   (a) introducing one or more nucleic acid analytes to a first reaction mixture comprising:
      i) a single-stranded probe oligonucleotide $A_0$ comprising a 3' end region complementary to the target polynucleotide sequence;
      ii) a pyrophosphorolysing enzyme; and
      iii) a ligase;

wherein the analyte anneals to the single-stranded probe oligonucleotide $A_0$ to create a first intermediate product which is at least partially double-stranded, and wherein the 3' end of $A_0$ forms a double-stranded complex with the analyte and wherein $A_0$ is pyrophosphorolysed in the 3'-5' direction from the 3' end to create at least a partially digested strand $A_1$ and $A_1$ undergoes ligation using a splint to form oligonucleotide $A_2$, wherein the target polynucleotide sequence functions as the splint or the splint includes an oligonucleotide D, and wherein undergoing ligation includes:

ligation of the 3' end of $A_1$ to the 5' end of $A_1$ to form a circular construct; or ligation of the 3' end of $A_1$ to a 5' end of a ligation probe oligonucleotide C; and (b) detecting a signal derived from products of step (a) and inferring therefrom the presence or absence of the target polynucleotide sequence in the analyte, wherein the products of step (a) comprise $A_2$, a portion of $A_2$, multiple copies of $A_2$, or multiple copies of a portion of $A_2$.

2. The method of claim 1, wherein the first reaction mixture further comprises a source of pyrophosphate ions.

3. The method of claim 1, wherein the first reaction mixture further comprises at least one single-stranded primer oligonucleotide that is substantially complementary to a portion of $A_0$ and deoxyribonucleotide triphosphates (dNTPs).

4. The method of claim 3, wherein the first reaction mixture further comprises an amplification enzyme.

5. The method of claim 3, wherein the dNTPs are hot start dNTPs.

6. The method of claim 1, wherein the products of step (a) are introduced to a second reaction mixture prior to step (b), said second reaction mixture comprising at least one single-stranded primer oligonucleotide and deoxyribonucleotide triphosphates (dNTPs).

7. The method of claim 6, wherein the second reaction mixture further comprises an amplification enzyme.

8. The method of claim 6, wherein the first or second reaction mixture further comprises the oligonucleotide D.

9. The method of claim 8, wherein D comprises an oligonucleotide region complementary to the 3' end of $A_1$ and a region complementary to either the 5' end of oligonucleotide C or to the 5' end of $A_1$.

10. The method of claim 8, wherein D is unable to undergo extension against $A_1$ by virtue of a 3' modification of D, or through a mismatch between the 3' end of D and the corresponding region of $A_1$.

11. The method of claim 1, wherein the partially digested strand $A_1$ is circularised through ligation of its 3' and 5' ends to create the oligonucleotide $A_2$.

12. The method of claim 11, wherein ligation occurs:
during step (a);
during step (b); or
between steps (a) and (b).

13. The method of claim 12, wherein the first reaction mixture further comprises a 5'-3' exonuclease, and wherein the 5' end of $A_0$ is resistant to 5'-3' exonuclease digestion.

14. The method of claim 1, wherein the first reaction mixture further comprises the ligation probe oligonucleotide C, and the partially digested strand $A_1$ is ligated at the 3' end to the 5' end of C to create the oligonucleotide $A_2$.

15. The method of claim 14, wherein ligation occurs:
during step (a);
during step (b); or
between steps (a) and (b).

16. The method of claim 15, wherein the first reaction mixture further comprises a 5'-3' exonuclease, and wherein the 5' end of $A_0$ is resistant to 5'-3' exonuclease digestion.

17. The method of claim 14, wherein the oligonucleotide C further comprises a 3' or internal modification protecting it from 3'-5' exonuclease digestion.

18. The method of claim 1, wherein the first reaction mixture further comprises a phosphatase or phosphohydrolase.

19. The method of claim 1, wherein prior to or during step (b), the products of step (a) are treated with a pyrophosphatase or an exonuclease.

20. The method of claim 1, wherein the first reaction mixture further comprises the oligonucleotide D.

21. The method of claim 20, wherein the splint includes the oligonucleotide D, and wherein D comprises an oligonucleotide region complementary to the 3' end of $A_1$ and a region complementary to either the 5' end of oligonucleotide C or to the 5' end of $A_1$.

22. The method of claim 21, wherein D is unable to undergo extension against $A_1$ by virtue of a 3' modification of D or through a mismatch between the 3' end of D and the corresponding region of $A_1$.

23. The method of claim 1, wherein the enzyme which performs pyrophosphorolysis of $A_0$ to form partially digested strand $A_1$ also amplifies $A_2$.

24. The method of claim 1, wherein detection is achieved using one or more oligonucleotide fluorescent binding dyes or molecular probes.

25. The method of claim 24, wherein an increase in signal over time resulting from the generation of amplicons of $A_2$ is used to infer a concentration of the target polynucleotide sequence in the analyte.

26. The method of claim 24, wherein step (b) comprises:
i) labelling the products of step (a) using one or more oligonucleotide fluorescent binding dyes or molecular probes;
ii) measuring the fluorescent signal of the labeled products;
iii) exposing the labeled products to a set of denaturing conditions; and
iv) identifying the target polynucleotide sequence in the analyte by monitoring changes in the fluorescent signal of the labeled products during exposure to the denaturing conditions.

27. The method of claim 1, wherein the first reaction mixture comprises multiple probes $A_0$, each selective for a different target polynucleotide sequence of the analyte and each including an identification region, wherein amplicons of $A_2$ include at least one of the identification regions, and wherein the presence of the target polynucleotide sequences present in the analyte are inferred through the detection of the identification regions.

28. The method of claim 27, wherein detection of the identification regions is carried out using molecular probes or through sequencing.

29. The method of claim 27, wherein the multiple probes $A_0$ comprise a common priming site, allowing a single or single set of primers to be used for amplification.

30. The method of claim 1, wherein the one or more nucleic acid analytes are split into multiple reaction volumes, each volume being introduced into a respective first reaction mixture having one or more probe oligonucleotides $A_0$ selective for different target polynucleotide sequences.

* * * * *

UNITED STATES PATENT AND TRADEMARK OFFICE
CERTIFICATE OF CORRECTION

PATENT NO. : 11,332,780 B2
APPLICATION NO. : 16/911762
DATED : May 17, 2022
INVENTOR(S) : Barnaby Balmforth et al.

It is certified that error appears in the above-identified patent and that said Letters Patent is hereby corrected as shown below:

On the Title Page

Item [57], Line 9, delete "pyrophosphorylsed" and insert --pyrophosphorolysed--.

Signed and Sealed this
Second Day of August, 2022

Katherine Kelly Vidal
*Director of the United States Patent and Trademark Office*

SEQUENCE LISTING

<160> NUMBER OF SEQ ID NOS: 6

<210> SEQ ID NO 1
<211> LENGTH: 69
<212> TYPE: DNA
<213> ORGANISM: Artificial Sequence
<220> FEATURE:
<223> OTHER INFORMATION: Synthetic DNA Sequence

<400> SEQUENCE: 1
atgttcgatg agctttgaca atacttgaag ctcgcagata taggatgttg cgatagtcca    60
ggaggctgc                                                            69

```
<210> SEQ ID NO 2
<211> LENGTH: 36
<212> TYPE: DNA
<213> ORGANISM: Artificial Sequence
<220> FEATURE:
<223> OTHER INFORMATION: Synthetic DNA sequence

<400> SEQUENCE: 2
tgtcaaagct catcgaacat cctggactat gtctcc                              36

<210> SEQ ID NO 3
<211> LENGTH: 75
<212> TYPE: DNA
<213> ORGANISM: Artificial Sequence
<220> FEATURE:
<223> OTHER INFORMATION: Synthetic sequence of Homo sapiens EGFR C797S

<400> SEQUENCE: 3
tgctgggcat ctgcctcacc tccaccgtgc agctcatcac gcagctcatg cccttcggca    60
gcctcctgga ctatg                                                     75

<210> SEQ ID NO 4
<211> LENGTH: 75
<212> TYPE: DNA
<213> ORGANISM: Artificial Sequence
<220> FEATURE:
<223> OTHER INFORMATION: Synthetic sequence of Homo sapiens EGFR

<400> SEQUENCE: 4
tgctgggcat ctgcctcacc tccaccgtgc agctcatcac gcagctcatg cccttcggct    60
gcctcctgga ctatg                                                     75

<210> SEQ ID NO 5
<211> LENGTH: 20
<212> TYPE: DNA
<213> ORGANISM: Artificial Sequence
<220> FEATURE:
<223> OTHER INFORMATION: Synthetic DNA sequence

<400> SEQUENCE: 5
tcgcaacatc ctatatctgc                                                20

<210> SEQ ID NO 6
<211> LENGTH: 20
<212> TYPE: DNA
<213> ORGANISM: Artificial Sequence
<220> FEATURE:
<223> OTHER INFORMATION: Synthetic DNA sequence

<400> SEQUENCE: 6
tgagctttga caatacttga                                                20
```